US007432101B2

(12) United States Patent
Guehenneux et al.

(10) Patent No.: US 7,432,101 B2

(45) Date of Patent: Oct. 7, 2008

(54) PRODUCTION OF POXVIRUSES WITH ADHERENT OR NON ADHERENT AVIAN CELL LINES

(75) Inventors: Fabienne Guehenneux, Le Temple de Bretagne (FR); Bertrand Pain, Clermont-Ferrand (FR)

(73) Assignee: Vivalis, Roussay (FR)

( * ) Notice: Subject to any disclaimer, the term of this patent is extended or adjusted under 35 U.S.C. 154(b) by 46 days.

(21) Appl. No.: 10/565,281

(22) PCT Filed: Jul. 22, 2004

(86) PCT No.: PCT/IB2004/002621

§ 371 (c)(1),
(2), (4) Date: Jan. 20, 2006

(87) PCT Pub. No.: WO2005/007840

PCT Pub. Date: Jan. 27, 2005

(65) Prior Publication Data

US 2006/0233834 A1 Oct. 19, 2006

(30) Foreign Application Priority Data

Jul. 22, 2003 (EP) .................................. 03291813
Dec. 9, 2003 (FR) .................................. 03 14389

(51) Int. Cl.
*C12N 7/00* (2006.01)
*A61K 39/285* (2006.01)
*C12N 5/00* (2006.01)

(52) U.S. Cl. .................................................. 435/235.1

(58) Field of Classification Search ...................... None
See application file for complete search history.

(56) References Cited

U.S. PATENT DOCUMENTS

2004/0058441 A1 3/2004 Pain et al.
2004/0170646 A1* 9/2004 Barban et al. ............ 424/199.1

FOREIGN PATENT DOCUMENTS

WO 03/076601 A1 9/2003

OTHER PUBLICATIONS

Hodge, JW. Carcinoembryonic antigen as a target for cancer vaccines. Cancer Immunol. Immunother. 1996; 43(1-2):127-134.*

Lovas B and Hollos I. Replication of vaccinia virus in the embryonated egg in the presence of methisazone. An electron=-microscopic study. Acta Microbiol Acad. Scient. Hungar. 1969; 16(1):47-62.*

Mayr, et al. The Smallpox Vaccination Strain MVA: Marker, Genetic Structure, Experience Gained with the Parenteral Vaccination and Behavior in Organism with a Debilitated Defence Mechanism. Abl. Bakt. Hyg., I. Abt. Org. B. 1978; 167:375-390.*

(Continued)

*Primary Examiner*—Mary E. Mosher
*Assistant Examiner*—Stuart W Snyder
(74) *Attorney, Agent, or Firm*—Buchanan, Ingersoll & Rooney, PC

(57) ABSTRACT

The present invention relates to a method for replicating pox viruses such as vaccinia virus comprising the steps of inoculating avian embryonic stem cells with viral particles and culturing said cells in a basal medium until cells lysis occurs and newly produced viral particles are released in said medium.

11 Claims, 12 Drawing Sheets

OTHER PUBLICATIONS

Figure 1:
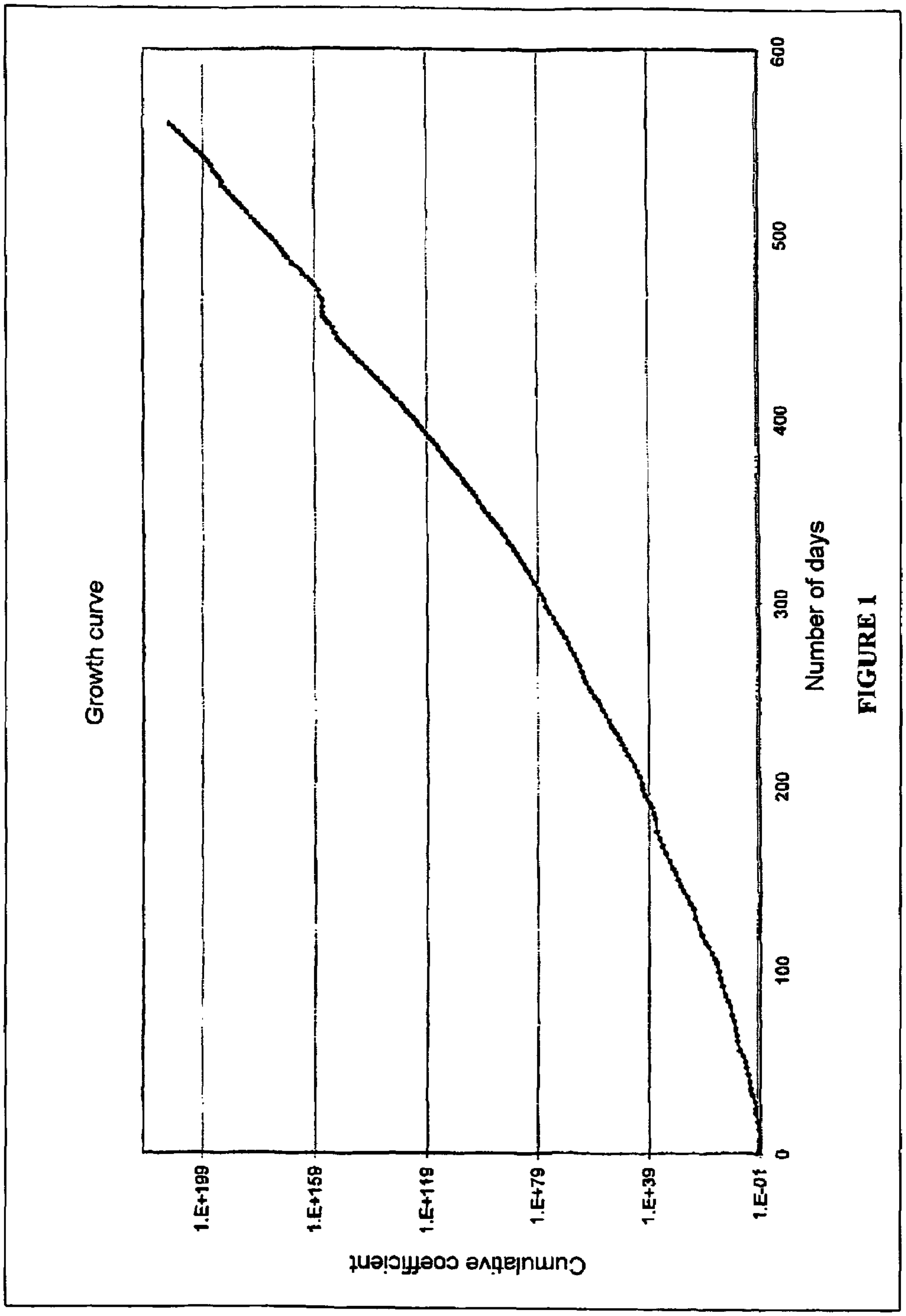

Pain, et al. Long-term in vitro culture and characterisation of avian embryonic stem cells with multiple morphogenetic potentialities. Development. 1996; 122:2339-2348.*

M Chabicovsky and P Ryle. Non-clinical development of cancer vaccines: Regulatory considerations.Regulatory Toxicology and Pharmacology 44 (2006) 226-237.*

Ferber, D. Monkey Virus Link to Cancer Grows Stronger. Science. May 10, 2002. vol. 296: 1012-1015.*

Pain, B., et al., "*Long-term in vitro culture and characterisation of avian embryonic stem cells with multiple morphogenetic potentialities*", Development Company of Biologists, 1996, pp. 2239-2348, vol. 122, No. 8, Cambridge, GB.

Drexler, I., et al., "*Highly attenuated modified vaccinia virus Ankara replicates in baby hamster kidney cells, a potential host for virus propagation, but not in various human transformed and primary cells*", Journal of General Virology, Feb. 1998, pp. 347-352, vol. 79, No. 2, Society for General Microbiology, Reading, GB.

Beug H., et al., "*Chicken Hematopoietic Cells Transformed by Seven Strains of Defective Avian Leukemia Viruses Display Three Distinct Phenotypes of Differentiation*," Cell, Oct. 1979, pp. 375-390, vol. 18, MIT.

Sugimoto M., et al., "*Characteristics of an attenuated vaccinia virus strain, LC16m0, and its recombinant virus vaccines*," Vaccine, 1994, pp. 675-681, vol. 12, No. 8, Butterworth-Heinemann Ltd.

Moss, "*Replicating and Host-Restricted Non-Replicating Vaccinia Virus Vectors for Vaccine Development*," Dev. Biol. Stand, 1994, pp. 55-63, vol. 82, S. Karger AG, Basel.

Smith J.R., et al., "*Replicative Senescence: Implications for in Vivo Aging and Tumor Suppression*," Science, Jul. 5, 1996, pp. 63-67, vol. 273.

Liu J.L., et al., "*Monoclonal Antibodies Recognizing Norman and Retrovirus-Transformed Chicken Hematopoietic Cells*," Virology, 1992, pp. 583-591, vol. 189, Academic Press Inc.

Guilhot C., et al., "*The 12S adenoviral E1A protein immortalizes avian cells and interacts with the avian RB product*," Oncogene, 1993, pp. 619-624, vol. 8, Macmillan Press Ltd.

Tartaglia J., et al., "*NYVAC:A Highly Attenuated Strain of Vaccinia Virus*," Virology, 1992, pp. 217-232, vol. 188, Academic Press, Inc.

Kawaguchi T., et al., "*Establishment and Characterization of a Chicken Hepatocellular Carcinoma Cell Line, LMH*[1]," Cancer Research, Aug. 15, 1987, pp. 4460-4464, vol. 47.

Samarut J., et al., "*Target Cells Infected by Avian Erythroblastosis Virus Differentiate and Become Transformed*," Cell, Apr. 1982, pp. 921-929, vol. 28, MIT.

Pain B., et al., "*Chicken Embryonic Stem Cells and Transgenic Strategies*," Cells Tissues Organs, 1999, pp. 212-219, vol. 165, S. Karger AG, Basel.

Eyal-Giladi H., et al., "*From Cleavage to Primitive Streak Formation: A Complementary Normal Table and a New Look at the First Stages of the Development of the Chick*," Developmental Biology, 1976, pp. 321-337, vol. 49, Academic Press, Inc.

Moscovici C., et al., "*Continuous Tissue Culture Cell Lines Derived from Chemically Induced Tumors of Japanese Quail*," Cell, May 1977, pp. 95-103, vol. 11, MIT.

Baha T., et al., "*Formation of a transformed follicle is necessary but not sufficient for development of an avian leukosis virus-induced lymphoma*," Proc. Natl. Acad. Sci., Jan. 1985, pp. 213-216, vol. 82, USA.

Blanchard T., et al., "*Modified vaccinia virus Ankara undergoes limited replication in human cells and lacks several immunomodulatory proteins: implications for use as a human vaccine*," Journal of General Virology, 1998, pp. 1159-1167, vol. 79, Great Britain.

Kempe C.H., et al., "*Smallpox Vaccination of Eczema Patients with a Strain of Attenuated Live Vaccinia* (*CVI-78*)," Pediatrics, Dec. 1968, pp. 980-985, vol. 42, No. 6, www.pediatrics.org.

Kim H., et al., "*Alterations in p53 and E2F-1 function common to immortalized chicken embryo fibroblasts*," Oncogene, 2001, pp. 2671-2682, vol. 20, Nature Publishing Group.

Kim H., et al., "*Post-transcriptional inactivation of p53 in immortalized murine embryo fibroblast cells*," Oncogene, 2001, pp. 3306-3310, vol. 20, Nature Publishing Group.

Pastoret, et al., "*Poxviruses as vaccine vectors*," Comparative Immunology, Microbiology & Infectious Diseases 26 (2003), pp. 343-355, published by Elsevier Science Ltd., Oxford, UK.

Zeh, et al., "*Development of a replication-selective, oncolytic poxvirus for the treatment of human cancers*," Cancer Gene Therapy (2002), 9, pp. 1001-1012, published by Nature Publishing Group, Houndsmills, Basingstoke, Hampshire, UK.

* cited by examiner

PRODUCTION OF POXVIRUSES WITH ADHERENT OR NON ADHERENT AVIAN CELL LINES

CROSS-REFERENCE TO RELATED APPLICATIONS

This application is the U.S. national stage of International Application No. PCT/IB2004/002621, filed Jul. 22, 2004, incorporated by reference herein in its entirety and relied upon, which claims priority under 35 U.S.C. §119 of Application No. 03291813.8, filed in the European Patent Office on Jul. 22, 2003 and Application No. 0314389, filed in France on Dec. 9, 2003.

The present invention relates to a method for producing live or attenuated pox viruses, in particular vaccinia viruses, native or modified, with avian cell lines, in particular avian embryonic stem cells, comprising infecting said cells with virus particles.

Historically, vaccinia virus is known to have been used successfully to immunize against smallpox allowing its eradication in 1980 according to the WHO. Since then, vaccination has been discontinued. Today, resurgence of this virus is considered as a potential threat that could be devastating for the unprotected population. The problem is that only 15 million doses of smallpox vaccine are available in the USA and the FDA has issued guidelines and contracts to produce large amounts of vaccine unit dose against smallpox. Further information are accessible at:

http://www.bt.cdc.gov/Agent/Smallpox/SmallpoxConsensus.pdf.

However, speeding-up production requires new production methods and suitable cell lines. In this invention, we describe new cell lines (adherent or non adherent) from avian species that could be used as substrate for vaccine production by pharmaceutical companies. These new cells are derived from avian embryos and could supersede eggs or primary embryo fibroblasts that are used at present.

Traditionally, vaccines induce immunity to diseases by using a weakened or inactivated version of the infectious agent. Today attenuated pox viruses properties like the absence of replication in human cells and the good induction of immune response allow the development of new vaccine strategies using for example MVA (Modified Virus Ankara) as vector. MVA is a highly attenuated strain of vaccinia virus (VV) that was initially developed as a safe vaccine for smallpox prior to eradication of that disease. MVA was derived from the Ankara strain by over 570 serial passages through primary chick embryo fibroblasts (CEF) and, as a consequence of this adaptation, contains several large genomic deletions compared to the parental strain. MVA can no longer replicate in most mammalian cell lines and is non pathogenic in animals. More importantly, no serious complications were reported when MVA was administered as a smallpox vaccine in more than 100,000 humans, including immuno-depressed individuals. By classical techniques of molecular biology, it is possible to obtain recombinant MVA containing foreign DNA coding for specific peptides or proteins of therapeutic interest. These recombinant viruses after injection, in vivo, are able to stimulate the immune system against specific antigens like tumoral antigens. At present, these new generations of vaccine vectors are developed or could be developed to fight against human or animal infectious diseases and against a wide variety of tumor types (melanoma, prostate cancer, breast cancer, lung cancer, ovary cancer, liver cancer . . . ).

Drexler I. et al. (1998 J. Gen Virol. 79:347-352) have observed that highly attenuated Modified Vaccinia virus Ankara (MVA) replicates in baby hamster kidney cells (a potential host for virus propagation) but not in various human transformed and primary cells; therefore, the host range of MVA is restricted. Moreover this highly attenuated poxvirus strain do not create productive infections (Moss B, Dev Biol Stand 1994:55-63). For example, Blanchard T J. et al. (1998 J. Gen. Virol. 79:1159-1167) have reported that Modified Vaccinia virus Ankara undergoes limited replication in human cells and lacks several immuno-modulatory proteins. In addition, production yields must be commensurate with economical viability of smallpox vaccine mass production.

The strong safety record of MVA and the potent cellular and humoral immune response elicited in vaccinated individuals has generated considerable scientific and industrial interest in the use of MVA as a recombinant vector to immunize against human and animal infectious diseases, in particular against HIV and cancer. Given its adaptation to CEF, MVA can be grown to high titers in such cells and current clinical batches of recombinant MVA vaccine candidates are produced on primary CEF. However, the establishment of CEFs requires experience in preparing primary tissue culture and depends on eggs from chicken kept under special pathogen-free conditions. Furthermore, the production process is enormously laborious and difficult to standardize, since primary cells survive only a few passages and have thus to be prepared continuously from embryonated eggs. While vaccine producers can deal with such limitations for the production of batches of MVA material for phase I and II clinical trials, scaling-up the CEF-based production process for phase III clinical trials and eventually for later product commercialization remains a serious hurdle.

The problem to be solved by the present invention is to provide cell lines for replicating the vaccinia virus which would obviate the above mentioned problems and which would meet with regulatory agency requirements. That's the purpose of the present invention.

Ideally, such a cell line should be fully regulatory compliant; the cell shall be fully characterized with a known history. Furthermore, the cell line shall be non tumorigenic, genetically unmodified, and stable under long-term culture. The cell line shall be able to replicate viruses and adapted to stable adherent and suspension growth in serum-free medium. In this regards, the inventors investigated the use of avian cells for replicating viruses. The inventors report that the established new avian embryonic derived stem cell lines detailed in our co-pending application PCT/FR03/00735 (WO03/076601), are particularly suitable for replicating poxviruses, in particular orthopoxvirus such as the vaccinia virus.

Because unlimited cell proliferation is required for the process of vaccine mass production, the inventors choose to examine the avian embryonic derived stem cell ability for replicating viruses. However, to maintain avian embryonic derived stem cells in vitro for long periods of time, it is necessary to observe specific culture and maintenance conditions as described in Pain et al. (1996, Development 122: 2339-2348); U.S. Pat. No. 6,114,168 and EP 787 180 and these culture conditions are cost demanding. The problem was to be able to maintain avian embryonic derived stem cells in culture in an economical medium while avoiding stumbling blocks such as cellular differentiation and senescence. In the context of the invention, it has been found that the withdrawal of growth factors, serum and/or feeder layer leads to the isolation of populations of avian embryonic derived stem cells, which can grow indefinitely in basic culture media.

Also, apart from the hematopoietic stem cells which are for the most part non-adherent cells, the cells obtained according to the prior art techniques exhibit an adherent phenotype. However, non-adherent cells are preferred for the industrial production of viral vaccines. This phenotype is advantageous both because of ease of handling which avoids the use of a proteolytic enzyme for dissociation and for the high cell densities reached by non-adherent cells cultured in vitro. The present invention describes the production of avian embryonic derived stem cell lines which can become spontaneously non-adherent or for which the non-adherence is obtained by a withdrawal of the feeder layer. Because of their growth in suspension, these lines are perfectly suitable for industrial production of vaccines in bioreactors.

In addition to their properties of growing on a basic culture medium, it has been discovered that these cell lines allow the replication of certain viruses in yields equivalent to or even higher than yields obtained with current methods, which makes these cells particularly useful for the mass production of vaccines.

DESCRIPTION

Thus, in a first aspect, the present invention relates to a method for replicating viruses, and more particularly vaccinia virus, such as native or recombinant vaccinia virus in avian embryonic derived stem cells. The method of the invention comprises the steps of inoculating said avian embryonic derived stem cells with viral particles and culturing said cells in a medium deprived in growth factors, feeder cells and/or animal serum, until cells lysis occurs and newly produced viral particles are released in said medium. Inoculation of avian stem cells of the invention is performed with an m.o.i. (multiplicity of infection) of 0.001 to 0.5, in a preferred embodiment of 0.01 to 0.5 and in a most preferred embodiment 0.01 to 0.1. This method is useful for producing vaccines, specially vaccines against poxviridae in particular against smallpox.

Said avian embryonic derived stem cell lines are obtainable by a process consisting of:

a) culturing avian cells, preferably avian embryonic, in a complete culture medium containing all the factors allowing their growth and a feeder layer, preferably inactivated, and complemented in serum;

b) passage by modifying the culture medium so as to obtain progressive or total withdrawal of said factors, of the serum and/or of the feeder layer, c) establishing adherent or non adherent avian cell lines capable of proliferating in a basal medium in the absence of exogenous growth factors, and/or inactivated feeder layer and/or a low level of serum or no serum;

In the event, the basal medium of step c) still comprises a low level of serum (i.e. around 2% or less), said process may optionally comprises an additional step d) of changing the basal medium containing no more exogenous growth factor, no more inactivated feeder layer and a low level of serum in a medium of culture selected among:

a basal medium complemented with serum (i) and diluted with a serum-free medium, then culturing during successive passages said avian cells in the basal medium (i) in which the ratio of serum-free medium is progressively increased up to the complete disappearance of said basal medium containing no exogenous growth factor, no inactivated feeder layer and a low level of serum;

a serum-free medium (SFM) complemented with serum (ii), then culturing during successive passages said avian cells in said medium (ii) in which the ratio of serum is progressively decreased up to the obtaining of a serum-free medium;

a serum-free medium (SFM) (iii), then culturing said avian cells in medium (iii); then maintaining in serum-free medium said avian cells adapted to the medium change.

The term <<avian>> as used herein is intended to refer to any species, subspecies or race of organism of the taxonomic class <<ava>>, such as, but not limited to, such organisms as chicken, turkey, duck, goose, quails, pheasants, parrots, finches, hawks, crows, ostrich, emu and cassowary. The term includes the various strains of *Gallus gallus,* or chickens (for example White Leghorn, Brown Leghorn, Barred-Rock, Sussex, New Hampshire, Rhode Island, Ausstralorp, Minorca, Amrox, California Gray, Italian Partidge-colored), as well as strains of turkeys, pheasants, quails, duck, ostriches and other poultry commonly bred. In a preferred embodiment, the avian cell of the present invention is a chicken cell.

The term "factor allowing their growth" as used herein meant growth factor necessary for the survival and the growth of the avian cells in culture. According to the invention, the growth factors comprises trophic factors and cytokines. Trophic factors are mainly SCF, IGF-1 and bFGF. Cytokines are mainly cytokines whose action is through a receptor which is associated with the gp130 protein such as LIF, interleukin 11, interleukin 6, interleukin 6 receptor, CNTF, oncostatin and cardiotrophin.

The avian cells of step a) are cells selected among avian embryonic cells, more preferably among avian embryonic stem cells and avian primary cells. In a preferred embodiment, the cells are totipotent or pluripotent avian embryonic stem cells isolated from a population suspension of dissociated stage X blastodermal cells obtained from an avian embryo, more preferably a chicken embryo (see EYAL-GILADI's classification: EYAL-GILADI and KOCHAN, 1976, <<From cleavage to primitive streack formation: a complementary normal table and a new look at the first stages of the development in the chick>>. "General Morphology" Dev. Biol. 49: 321-337). These avian embryonic stem cells are characterized by a slow doubling time comprises between 48 to 72 hours in culture at 39° C.

The modification of the culture medium of step b) of the process of the invention, so as to obtain progressive or total withdrawal of growth factors, serum and/or feeder layer, can be made simultaneously, successively or separately. The sequence of the weaning of the culture medium may be chosen among:

feeder layer/serum/growth factors;
feeder layer/growth factors/serum;
serum/growth factors/feeder layer;
serum/feeder layer/growth factors;
growth factors/serum/feeder layer,
growth factors/feeder layer/serum.

In a preferred embodiment, the sequence of the weaning is growth factors/feeder layer/serum.

In a particular embodiment, the invention relates to a method as defined above, in which the established lines are adherent stem cells which proliferate in the absence of inactivated feeder layer. In this regard, in the method described above, step b) consists in a withdrawal of the components of the medium (growth factors alone or serum alone or growth factors and then serum or alternatively serum and then growth factors).

In another embodiment, the invention relates to a method as defined above in which the established lines are non adherent stem cells which proliferate in suspension in a medium free of exogenous growth factors. In this regard, in the method described above, step b) consists in a progressive or total withdrawal of the feeder layer and then optionally in a withdrawal of the other components of the medium (growth factors and serum).

In another embodiment, the invention relates to a method as described above in which the established lines are non adherent stem cells which proliferate in suspension in a medium free of serum (serum-free medium).

In another embodiment, the invention relates to a method as defined above, in which the established lines are non adherent stem cells which proliferate in suspension in a medium free of exogenous growth factors and serum.

In another alternative, step b) consists in a progressive or total withdrawal of the growth factors, optionally followed by a progressive withdrawal of the serum.

In another alternative, step b) consists in a progressive or total withdrawal of the growth factors and/or serum, optionally followed by a withdrawal of the feeder layer.

In addition, the established lines may be cells which proliferate in a serum-depleted medium, in particular in a medium free of serum. The expression serum-depleted is understood to mean a gradual reduction of the concentration of serum spread out over time. This method allows a selection of clones which adapt to these new, increasingly drastic conditions until stable lines are obtained which are capable of growing in a serum-depleted medium or in a medium completely free of serum.

More precisely, step a) of the process comprises the seeding of culture flasks with around between $7\times10^4/cm^2$ to $8\times10^4/cm^2$ avian cells in a complete culture medium. Preferably, the seeding is made with around $7.3\times10^4/cm^2$ ($4\times10^6$ cells/55 $cm^2$ or $4\times10^6$ cells/100 mm dish).

By "complete culture medium", it is meant a basal medium complemented with growth factors and animal serum. Example of complete culture medium is described in Pain et al. (1996, Development 122:2339-2348), EP787,180 and U.S. Pat. No. 6,114,168, 5,340,740, 6,656,479 and 5,830,510. According to the invention, "basal medium" meant a medium with a classical media formulation that allows, by itself, at least cells survival, and even better, cell growth. Examples of basal media are BME (basal EagleMedium), MEM (minimum Eagle Medium), medium 199, DMEM (Dulbecco's modified Eagle Medium), GMEM (Glasgow modified Eagle medium), DMEM-HamF12, Ham-F12 and Ham-F10, Iscove's Modified Dulbecco's medium, MacCoy's 5A medium, RPMI 1640. Basal medium comprises inorganic salts (for examples: $CaCl_2$, KCl, NaCl, $NaHCO_3$, $NaH_2PO_4$, $MgSO_4$, . . . ), aminoacids, vitamins (thiamine, riboflavin, folic acid, D-Ca panthothenate, . . . ) and others components such as glucose, beta-mercaptoethanol, sodium pyruvate.

It is possible to schematically distinguish two families of growth factors: the cytokines and the trophic factors. The cytokines are mainly cytokines whose action is through a receptor which is associated with the gp130 protein. Thus, LIF, interleukin 11, interleukin 6, interleukin 6 receptor, CNTF, oncostatin and cardiotrophin have a similar mode of action with the recruitment at the level of the receptor of a specific chain and the combination of the latter with the gp130 protein in monomeric or sometimes heterodimeric form. The trophic factors are mainly SCF, IGF-1 and bFGF. More preferably, the complete medium comprises basal medium, Insulin Growth factor 1 (IGF-1), Ciliary Neurotrophic factor (CNTF), Interleukine 6 (IL-6), interleukine 6 receptor (IL-6R), Stem cell Factor (SCF), basic Fibroblast Growth Factor (bFGF), optionally interleukine 11 (IL-11) and animal serum.

The avian cells, preferably the avian embryonic cells of step a) are cultured during several passages in the complete medium. The medium is complemented by at least one of the growth factors selected in the group of: LIF, IGF-1, CNTF, IL-6, IL-6R, SCF, bFGF, IL-11, oncostatin, cardiotrophin.

According to a preferred embodiment, the complete culture medium is basal medium complemented with IGF-1, CNTF, IL-6, IL-6R, SCF, bFGF, optionally IL-11. The concentration of growth factors IGF-1, CNTF, IL-6, IL-6R, SCF, bFGF, optionally IL-11 in the basal medium is comprised between about 0.01 to 10 ng/ml, preferably, 0.1 to 5 ng/ml, and more preferably about 1 ng/ml.

After around passages 3 to 10, the complete medium is depleted in growth factors (step b). Preferably, for each growth factor, the depletion is made directly in one step, from one passage to another. Alternatively, the growth factor depletion is performed gradually, by a progressive decrease of the growth factor concentration in the complete medium. In a more preferred embodiment, the growth factors depletion is performed simultaneously for at least two growth factors. In a preferred embodiment, the depletion in growth factors is made in two rounds of depletion: firstly, SCF, IL6, IL6R, optionally IL11 are directly removed from the complete medium; the avian cells are then maintained in culture for at least one passage in a complete medium containing IGF1 and CNTF, optionally IL-11, and supplemented with animal serum. Secondly, IGF1 and CNTF, optionally IL-11 are directly removed from the culture medium, which ultimately comprises the basal medium only supplemented with serum. Usually, the medium is totally depleted in growth factors at around passages 20 to 30.

In a preferred embodiment, the deprivation of feeder cells is performed after the deprivation of growth factors. The deprivation of feeder cells is progressive and performed over several passages. The avian cells are now seeded in flask at a lower concentration than in step a), about around $4\times10^4$ cell/$cm^2$ to $5\times10^4$ cell/$cm^2$. The feeder cells are seeded in flask at around $4.2\times10^4$ cell/$cm^2$. Progressively, the concentration of the feeder cells in the flask is decreased. Practically, the same concentration of the feeder cells is used for 2 to 4 passages, then a lower concentration of the feeder cells is used for an additional 2 to 4 passages, and so. The flask is then seeded with around $4.2\times10^4$ feeder cells/$cm^2$, then around $2.2\times10^4$ feeder cells/$cm^2$, then around $1.8\times10^4$ feeder cells/$cm^2$, then around $1.4\times10^4$ feeder cells/$cm^2$, then around $1.1\times10^4$ feeder cells/$cm^2$, then around $0.9\times10^4$ feeder cells/$cm^2$, then around $0.5\times10^4$ feeder cells/$cm^2$. Then the flask is seeded with $6.5\times10^4$ avian cells/$cm^2$ to $7.5\times10^4$ avian cells/$cm^2$ and without feeder cells. In the hypothesis that avian cells are not in good shape following a decrease of feeder cells concentration in the flask, then the avian cells are cultured for additional passages with the same feeder cells concentration before to pursue the feeder cells deprivation.

In another preferred embodiment, the serum deprivation is performed after the growth factor and the feeder cells deprivation. The basal medium is changed by a medium selected among:

- The basal medium (i) complemented with serum and diluted with a novel serum free medium (ii). Then the avian cells are cultured through successive passages in the medium (i) in which the serum free medium proportion is progressively increased up to the complete disappearing of the basal medium complemented in serum (progressive dilution).
- A novel serum free medium (ii) complemented with serum. Then the avian cells are cultured through successive passages in the medium (ii) in which the serum proportion is progressively decreased up to the obtaining of a serum-free medium (progressive weaning).

A novel serum free medium (ii) non complemented with serum. Then the avian cells are directly in the serum-free medium (ii) (direct weaning).

In a preferred embodiment, the serum deprivation is performed by progressive weaning.

In a first embodiment, the method of serum deprivation proce

According to the present invention, "serum-free medium" (SFM) meant a cell culture medium ready to use, that is to say that it does not required serum addition allowing cells survival and cell growth. This medium is not necessary chemically defined, and may contained hydrolyzates of various origin, from plant for instance. Preferably, said SFM are "non animal origin" qualified, that is to say that it does not contain components of animal or human origin (FAO status: "free of animal origin"). In SFM, the native serum proteins are replaced by recombinant proteins. Alternatively SFM medium according to the invention does not contain protein (PF medium: "protein free medium") and/or are chemically defined (CDM medium: "chemically defined medium"). SFM media present several advantages: (i) the first of all being the regulatory compliance of such media (indeed there is no risk of contamination by adventitious agents such as BSE, viruses); (ii) the optimization of the purification process; (iii) the better reproducibility in the process because of the better defined medium. Example of commercially available SFM media are: VP SFM (InVitrogen Ref 11681-020, catalogue 2003), Opti Pro (InVitrogen Ref 12309-019, catalogue 2003), Episerf (InVitrogen Ref 10732-022, catalogue 2003), Pro 293 S-CDM (Cambrex ref 12765Q, catalogue 2003), LC17 (Cambrex Ref BESP302Q), Pro CHO 5-CDM (Cambrex ref 12-766Q, catalogue 2003), HyQ SFM4CHO (Hyclone Ref SH30515-02), HyQ SFM4CHO-Utility (Hyclone Ref SH30516.02), HyQ PF293 (Hyclone ref SH30356.02), HyQ PF Vero (Hyclone Ref SH30352.02), Ex cell 293 medium (JRH Biosciences ref 14570-1000M), Ex cell 325 PF CHO Protein free medium (JRH Biosciences ref 14335-1000M), Ex cell VPRO medium (JRH Biosciences ref 14560-1000M), Ex cell 302 serum free medium (JRH Biosciences ref 14312-1000M).

The invention also relates to a process of obtaining avian cell lines, preferably non transformed cell lines, able to grow in serum-free medium; those cell lines are cultured in a complete culture medium optionally with feeder cells. Said process comprises the steps of:

culturing the avian cell, preferably non-transformed, in a complete culture medium and optionally with feeder layer. The avian cell may be the avian cells of step a) above, the established avian cell lines of the process of the invention, such as EB1, EB14 or S86N45 (also named EB45), or other avian embryonic derived cell line such as DF1 (U.S. Pat. Nos. 5,672,485 and 6,207,415);

at least one passage in culture by modifying or changing the culture medium in order to obtain a total weaning of serum, either by progressive or direct withdrawal of serum;

establishing adherent or non-adherent avian cell lines able to grow in serum-free medium.

The instant invention relies on the finding that the passage from a basal cell culture medium complemented with animal serum to a serum-free medium shall not be performed by the simple removal of the serum from the basal culture medium but shall need a change in the type of the culture medium, that should be a serum-free medium (SFM). Moreover, when the avian cell lines necessitate to be grown with growth factors or feeder cells, the serum weaning is preferably performed after the weaning in growth factors and/or feeder cells.

The feeder cells are animal cells that have been preferably inactivated by irradiation or chemically treated with mitomycin. The feeder may be genetically modified to express growth factors such as SCF. Preferably, the feeder cells are mouse fibroblasts cell lines such as STO (American Type Culture Collection ATCC N°CRL-1503).

The method described above may additionally comprise a step in which the cells obtained in step c) are subjected to a selection or an adaptation in culture media used for large-scale production so as to obtain clones suitable for the production of vaccines intended for human or animal therapy.

This process leads to the establishment of new avian embryonic derived cell lines which are maintained in culture in vitro over a considerable period of time. Advantageously, the cells derived from the cell lines obtained in step c) are capable of proliferating for at least 50 days, 100 days, 150 days, 300 days or preferably at least 600 days. The 600 days do not constitute a time limit because the cell lines obtained are still alive after much longer time periods. Hence, these lines are considered as being able to grow indefinitely in a basic culture medium free of exogenous growth factors, serum and/or inactivated feeder layer. The expression "line" is understood to mean any population of cells capable of proliferating indefinitely in culture in vitro while retaining to a greater or lesser degree the same morphological and phenotypic characteristics. Of course, the method mentioned above makes it possible to obtain cellular clones derived from cells obtained from established lines. These clones are cells which are genetically identical to the cell from which they are derived by division.

The established cell lines and the cells derived thereof (step c or d) are preferably embryonic derived avian stem cells lines, more precisely those cells are pluripotent avian embryonic derived stem cells. The avian embryonic derived stem cells obtainable by the process of the invention are small, round, individualized cells with a doubling time of around 24 hours or less at 39° C. The cells obtainable by the process of the invention are at least at passage p60, at least p70, at least p80, at least p90, at least p100, at least p110 at least p120 or at least p130 or later. The avian embryonic derived stem cells according to the invention have at least one of the following characteristics:

a high nucleo-cytoplasmic ratio, an endogenous alkaline phosphatase activity, an endogenous telomerase activity, a reactivity with specific antibodies selected from the group of antibodies SSEA-1 (TEC01), SSEA-3, and EMA-1.

A doubling time shorter than the doubling time of the avian cells of step a) of the process of the invention (48 to 72 h at 39° C.), of about 24 hours or less in the same culture conditions.

These cell lines and the cells derived there from are capable of proliferating for at least 50 days, 100 days, 150 days, 300 days, or preferably at least 600 days in a basal medium, in particular in a medium such as DMEM, GMEM, HamF12 or McCoy supplemented with various additives commonly used by persons skilled in the art. Among the additives, there may be mentioned non-essential amino acids, vitamins and sodium pyruvate. However, the cells are able to proliferate in basal medium without glutamine.

These cells lines and the cells derived there from have the characteristic to grow either as adherent cells or as suspension cells.

Preferably, the cells of the invention have all the above mentioned characteristics.

The avian established cell lines of the invention and the cells derived thereof are useful for the production of biologics such as recombinant peptides and proteins (i.e antibodies, hormones, cytokines . . . ), viruses, viral vectors, viral particles and viral vaccines.

More precisely, the avian established cell lines of the invention and the cells derived thereof are useful for the replication of viruses and/or related vectors and particles for the production of live or attenuated, recombinant or not, vaccines against diseases, such cancers and infectious diseases. The viruses, the related viral vectors, the viral particles and viral vaccines are preferably chosen among the group of adenoviruses, hepadnaviruses, herpes viruses, orthomyxoviruses, papovaviruses, paramyxoviruses, picornaviruses, poxviruses, reoviruses and retroviruses. In a preferred embodiment, the viruses, the related viral vectors, viral particles and viral vaccines belong to the family of poxviruses, and more preferably to the chordopoxviridae. More preferably, the virus or the related viral vectors, viral particles and viral vaccines is an avipoxvirus selected among fowlpox virus, canary pox virus (i.e ALVAC), juncopox virus, mynahpox virus, pigeonpox virus, psittacinepox virus, quailpoxvirus, sparrowpoxvirus, starling poxvirus, turkey poxvirus. According to another preferred embodiment, the virus is vaccinia virus.

In another embodiment, the viruses, the related viral vectors, the viral particles and vaccines belong to the family of orthomyxoviruses, in particular influenza virus and to the family of paramyxoviruses, in particular measles, mumps and rubella viruses.

The invention also relates to the biologics, in particular the proteins and the vaccines, expressed and/or produced in the avian established cell lines of the invention.

In a preferred embodiment, the invention is related to the use of the adherent or non-adherent avian established cell lines of the invention, that are genetically, biologically or chemically unmodified, capable of proliferating indefinitely in culture, and having the above characteristics to replicate live or attenuated viruses of the orthopoxvirus family, more particularly live or attenuated vaccinia virus and recombinant vaccinia viruses.

The invention is aimed at the use of the adherent or non-adherent cells as defined above to produce live or attenuated vaccines comprising culturing the adherent or non adherent cell lines established in step c) or d) according to the process described above, inoculating said cells with viral particles and culturing said cells in a basal medium as mentioned above until cell lysis occurs and, recovering the newly produced viral particles released in said medium. The invention is particularly useful for the production of attenuated virus belonging to the family of orthopoxvirus, in particular vaccinia virus, Lister-Elstree vaccinia virus strain, modified vaccinia virus such as Modified Vaccinia virus Ankara (MVA) which can be obtained from ATCC (ATCC Number VR-1508), NYVAC (Tartaglia et al., 1992 Virology 188: 217-232), LC16 m8 (Sugimoto et Yamanouchi 1994 Vaccine 12:675-681), CVI78 (Kempe et al., 1968 Pediatrics 42: 980-985) and other recombinant vaccinia virus. Advantageously, the cells derived from established lines are infected in order to produce a live vaccinia virus or an attenuated virus which is a modified vaccinia virus and/or recombinant vaccinia. Said cells may be infected by any technique accessible to persons skilled in the art.

Alternatively, the cells derived from established lines are transfected or modified in order to produce a live vaccinia virus or an attenuated virus which is a modified vaccinia virus and/or recombinant vaccinia. Said cells may be modified by any technique accessible to persons skilled in the art, in particular by non homologous or homologous, directed and/or conditional recombination (Cre-Lox or FLP-FRT system), by transformation with any vector, plasmid, viruses or recombinant viruses in particular with the aid of retroviruses or recombinant retroviruses.

In one particular embodiment, the invention is directed to a method to produce live or attenuated vaccines such as a vaccine against smallpox comprising culturing the adherent or non adherent cell lines established in step c) or d) according to the process described above, inoculating said cells with viral particles and culturing said cells in a basal medium as mentioned above until cell lysis occurs and, recovering the newly produced viral particles released in said medium. The invention is particularly useful for the production of attenuated virus belonging to the family of poxvirus, in particular vaccinia virus, Lister-Elstree vaccinia virus strain, modified vaccinia virus such as Modified Vaccinia virus Ankara (MVA) which can be obtained from ATCC (ATCC Number VR-1508), NYVAC (Tartaglia et al., 1992 Virology 188: 217-232), LC16 m8 (Sugimoto et Yamanouchi 1994 Vaccine 12:675-681), CVI78 (Kempe et al., 1968 Pediatrics 42: 980-985) and others recombinant vaccinia viruses. For example, one can use MVA such as a vaccine against smallpox.

In a second particular embodiment, the invention is directed to a method to produce live or attenuated vaccines such as a vaccine against diseases, more preferably, acquired or infectious diseases; said method is comprising culturing the adherent or non adherent cell lines established in step c) or d) according to the process described above, inoculating said cells with viral recombinant particles and culturing said cells in a basal medium as mentioned above until cell lysis occurs and, recovering the newly produced viral recombinant particles released in said medium. For example, one can use recombinant MVA to express antigen against:

- acquired diseases such as, for example and without limitation, prostate cancer, pancreatic cancer, colorectal cancer, lung cancer, breast cancer, melanoma;
- infectious diseases such as, for example and without limitation, AIDS (HIV virus), hepatitis A, hepatitis B, hepatitis C, malaria, rabies, yellow fever, Japanese encephalitis, mumps, measles, rubella.

The vaccines produced by the above method are part of the present invention.

For the remainder of the description, reference will be made to the legend to the figures below.

LEGEND OF FIGURES

FIG. 1: Growth curve for one cell line of the invention showing the long term replication of cells.

Figure 2:
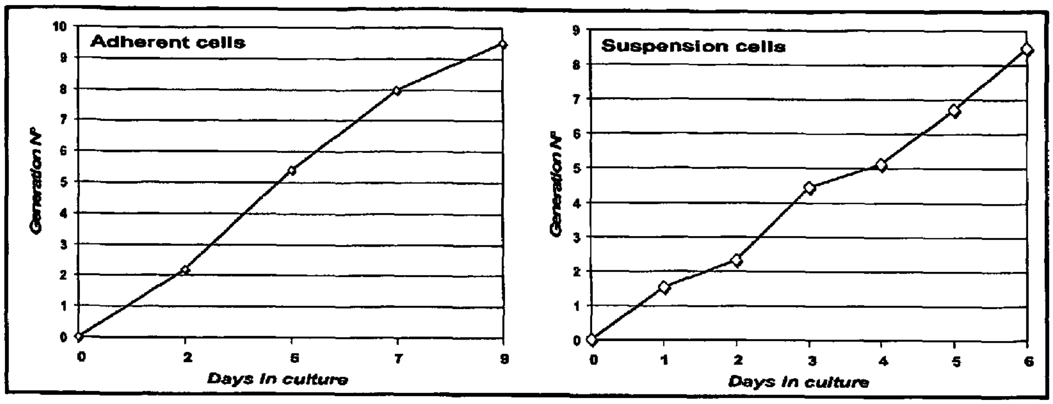

FIG. 2: population doubling times of S86N45 (EB45) (adherent) and EB14 (suspension) cells.

Figure 3:
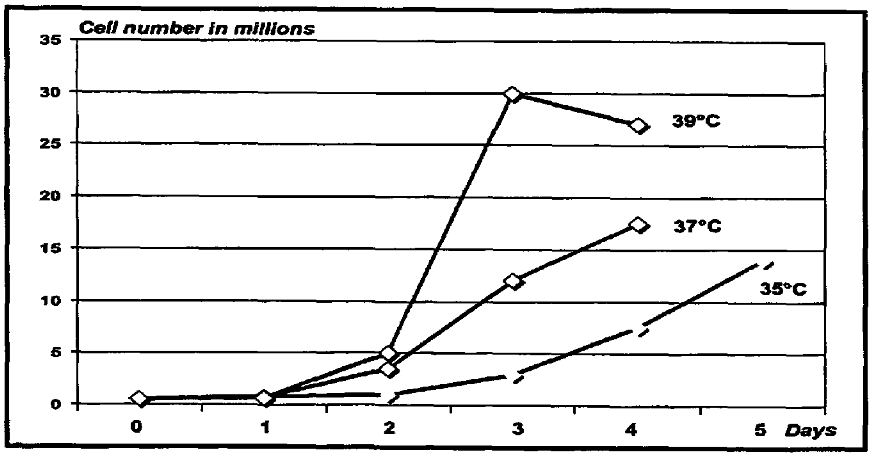

FIG. 3: influence of temperature on S86N45 (EB45) cells growth kinetics

Figure 4:
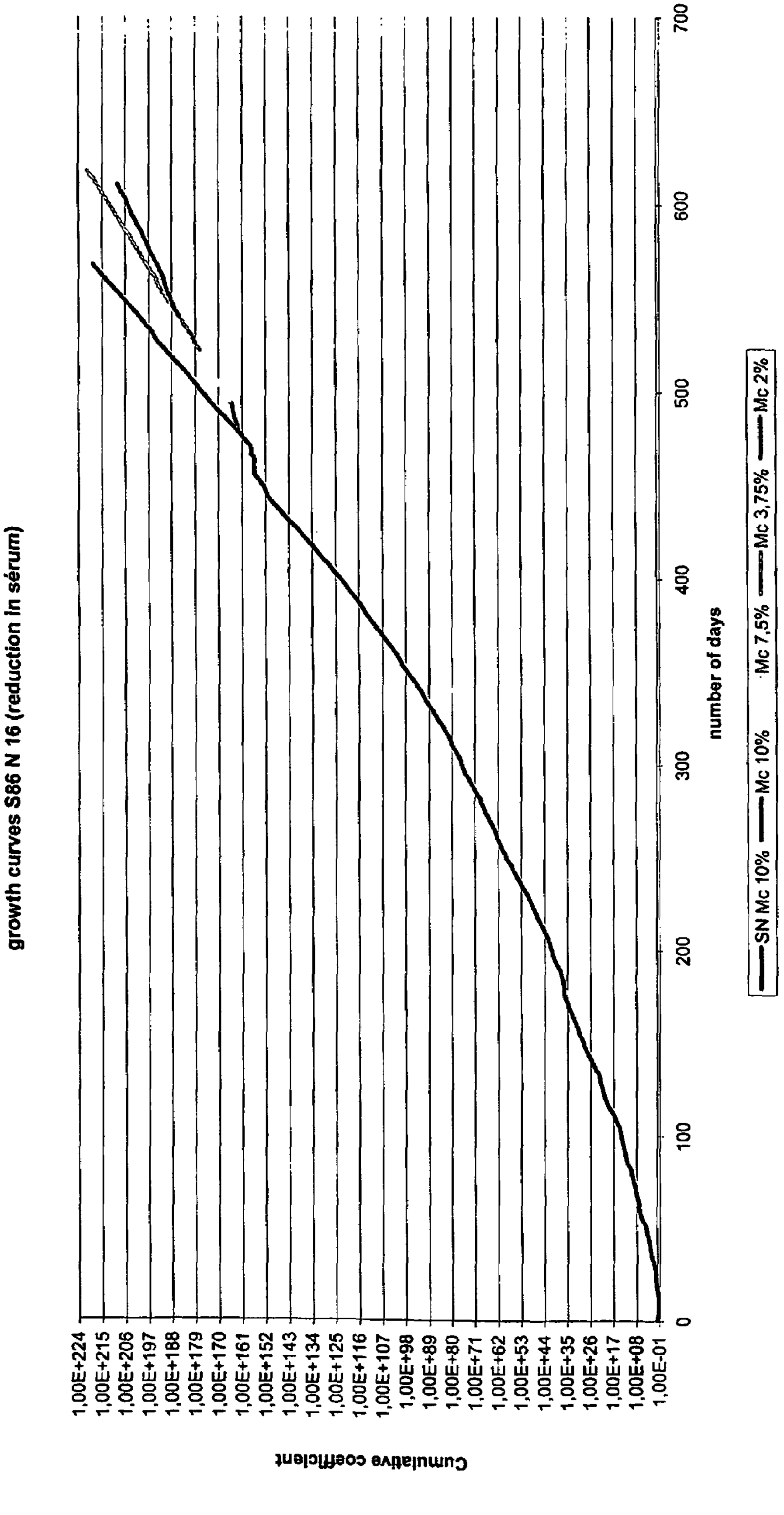

FIG. 4: Growth curve for one cell line of the invention showing the long term replication of cells with withdrawal of serum (up to 2% of serum).

Figure 5:
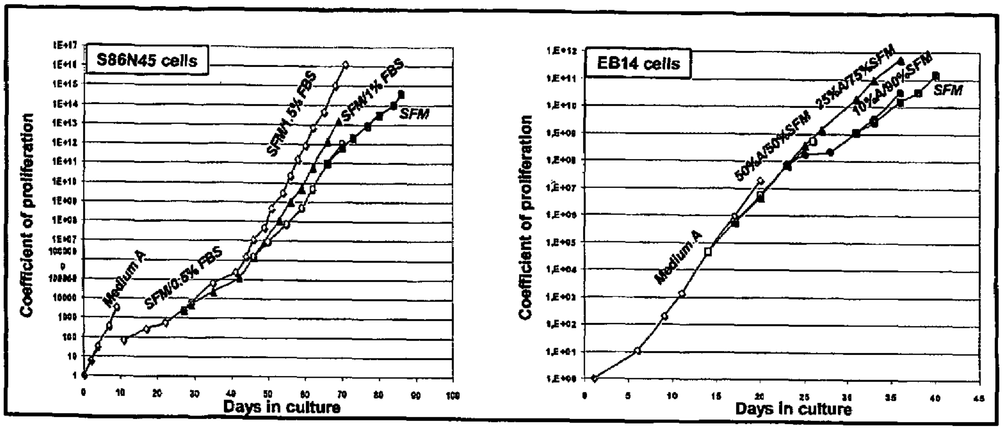

FIG. 5: Adaptation of S86N45 (EB45) and EB14 cells to growth in serum-free medium (SFM).

Figure 6:
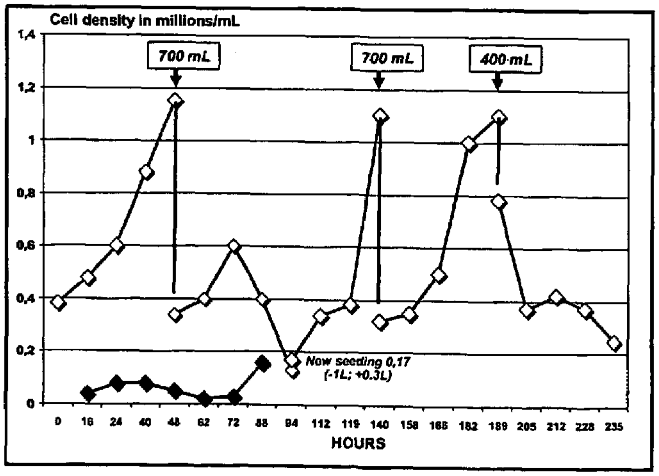

FIG. 6: Culture of EB14 suspension cells in a 2 L bioreactor in serum-free medium.

Figure 7:
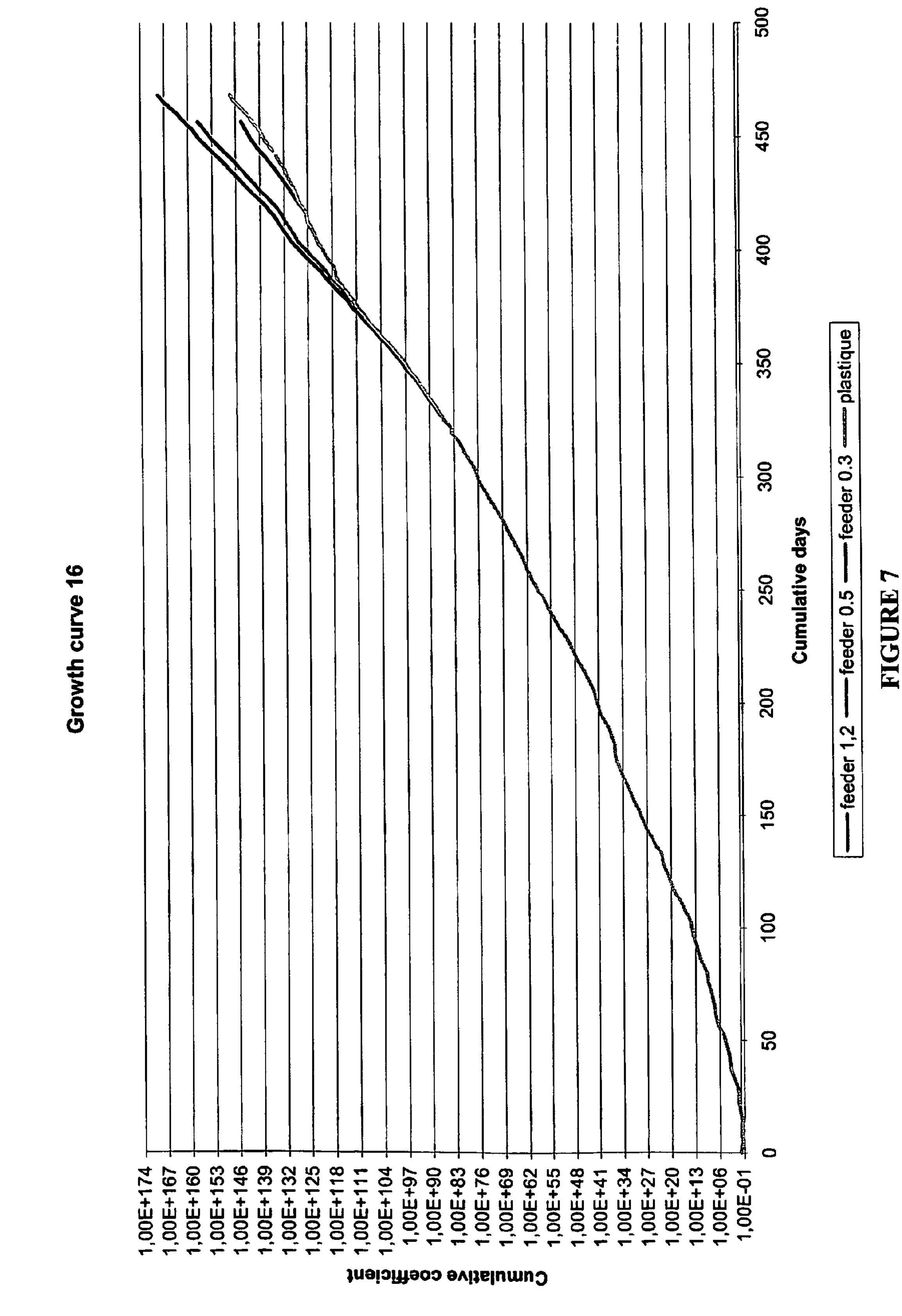

FIG. 7: Growth curve for one cell line of the invention (S86N16) showing the long term replication of cells with withdrawal of feeder layer.

Figure 8:

FIG. 8: Photograph showing the characteristic morphology of avian stem cells N: nucleus, n: nucleolus and C: cytoplasm (isolate S86N99, ×40 magnification, photograph taken with a Sony Cyber-shot digital camera)

Figure 9A:
Figure 9B:
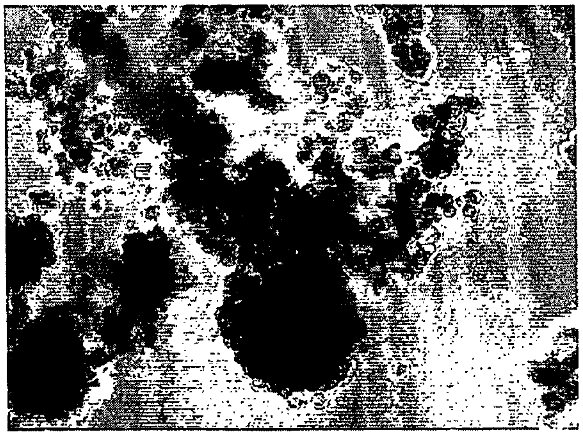

FIG. 9: Photographs showing the alkaline phosphatase activity of avian stem cell lines which are adherent or which are in suspension After fixing (0.1% formaldehyde/0.5% glutaraldehyde, 30 minutes at 4° C.), the cells are rinsed twice in 1×PBS and incubated for between 10 and 30 minutes at 37° C. in an NBT/BCIP (Nitro Blue Tetrazolium chloride 0.375 mg/ml, 5-bromo-4-chloro-3-indolyl phosphate 0.188 mg/ml, 0.1M Tris pH 9.5, 0.05M $MgCl_2$, 0.1M Nacl) solution. The reaction is stopped by two 1×PBS washes and the photographs are taken. A—illustrates the characteristic violet coloration of the endogenous alkaline phosphatase activity obtained with the adherent line S86N45 p87, a line cultured with no feeder or factor (×40 magnification, Sony Cyber-shot digital camera). B—illustrates the violet coloration characteristic of the endogenous alkaline phosphatase activity obtained with the EB14 line maintained from 8 passages in suspension, line derived from the S86N45 cells, cultured in suspension with no feeder or factor (×20 magnification, Sony Cyber-shot digital camera). C—S86N45 (EB45) cell-specific markers.

Figure 10:
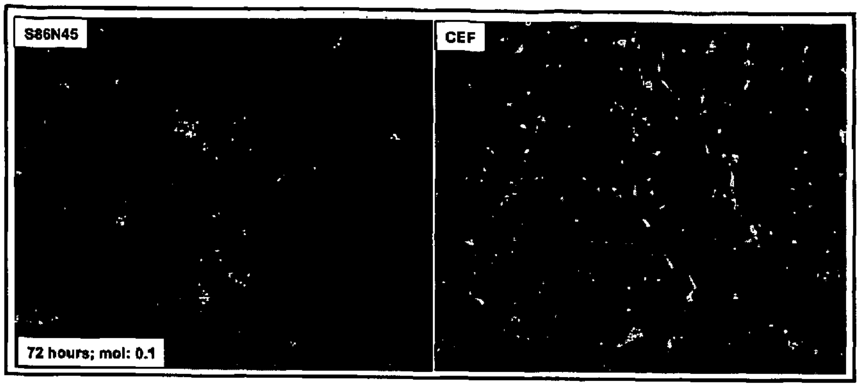

FIG. 10: Viral susceptibility of CEF and adherent S86N45 (EB45) cells (72 hours post-infection—MOI 0.1)

Figure 11:
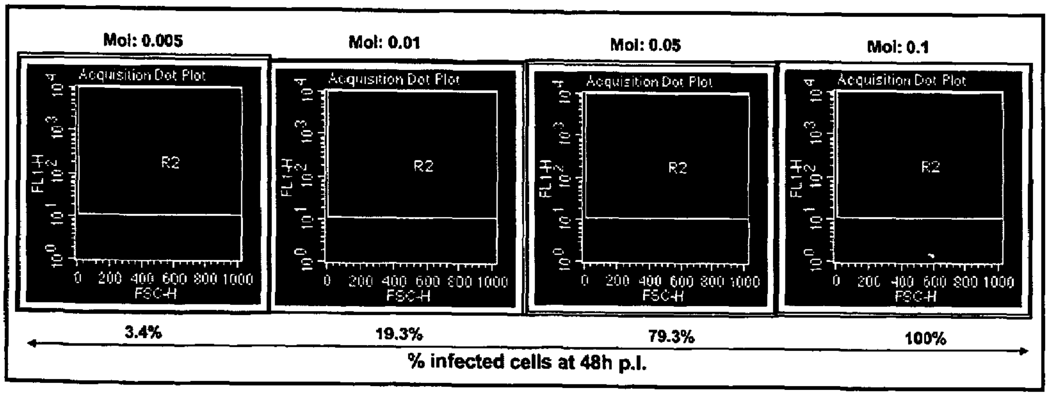

FIG. 11: Viral susceptibility of CEF and adherent S86N45 (EB45) cells at various multiplicity of infection (MOI) (48 hours post infection)

Figure 12:
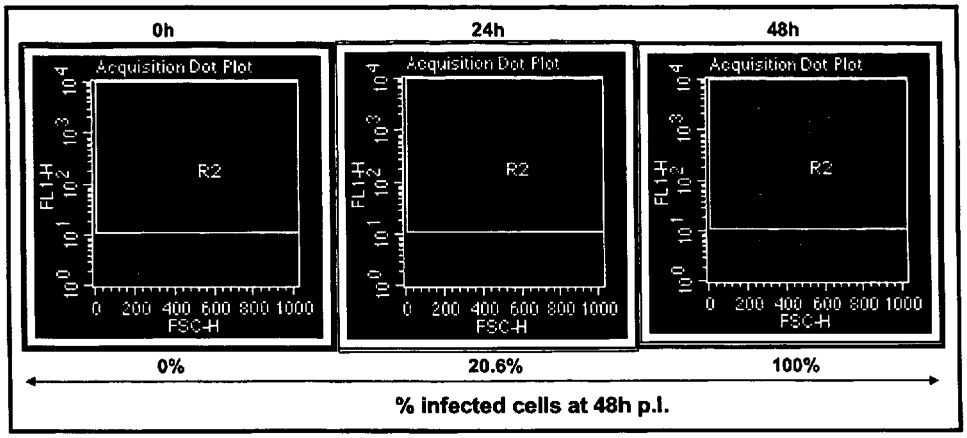

FIG. 12: kinetics of MVA-GFP propagation on adherent S86N45 (EB45) cells.

Figure 13:
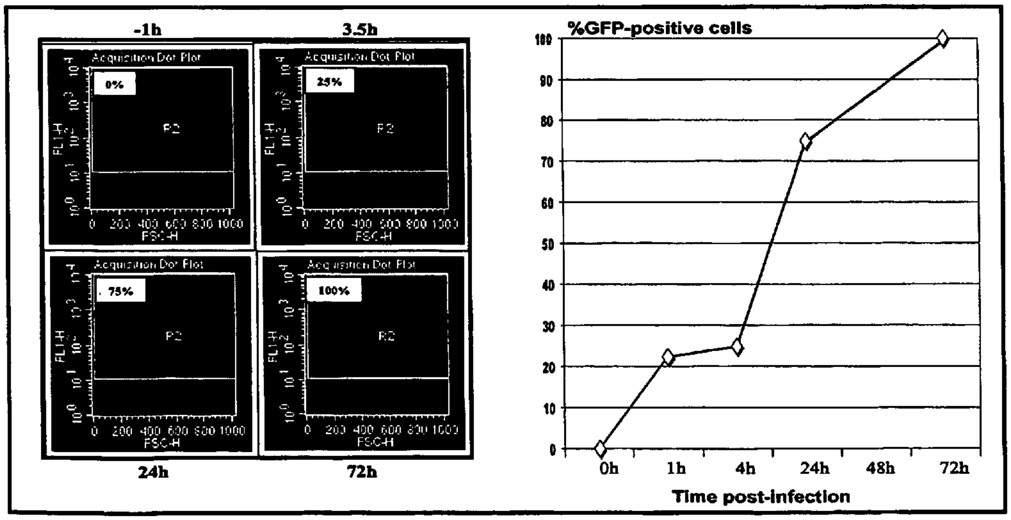

FIG. 13: kinetics of MVA-GFP propagation on suspension EB14 cells.

Figure 14:
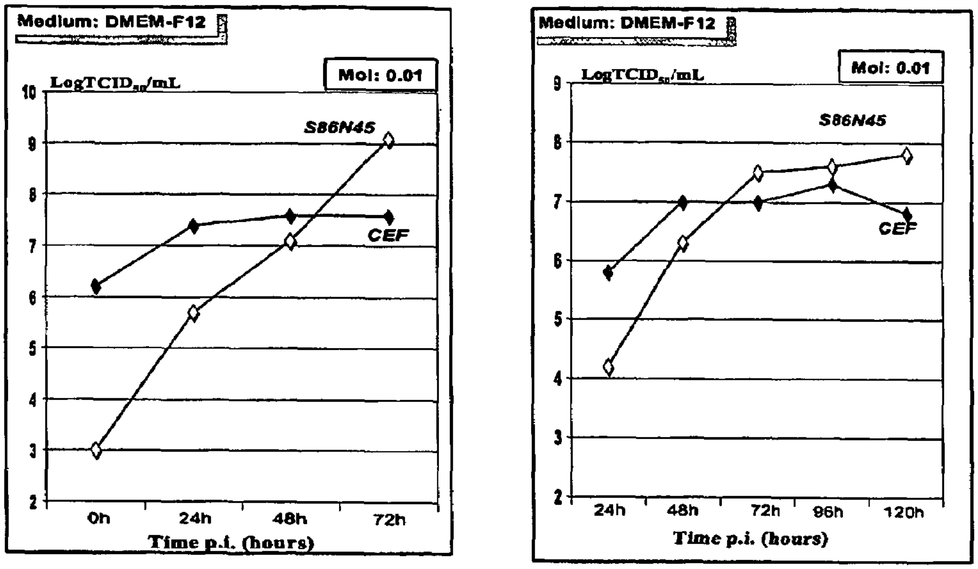

FIG. 14 MVA-GFP replication on S86N45 (EB45) cells grown on DMEM-F12 medium.

Figure 15:
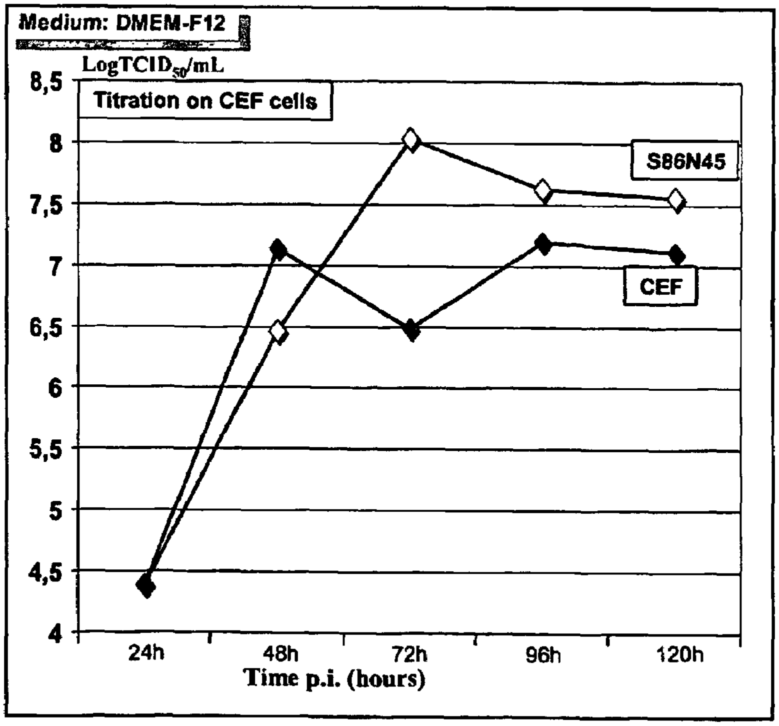

FIG. 15: Replication of a wild type MVA virus on S86N45 (EB45) cells grown on DMEM-F12 medium (MOI: 0.1)

Figure 16:
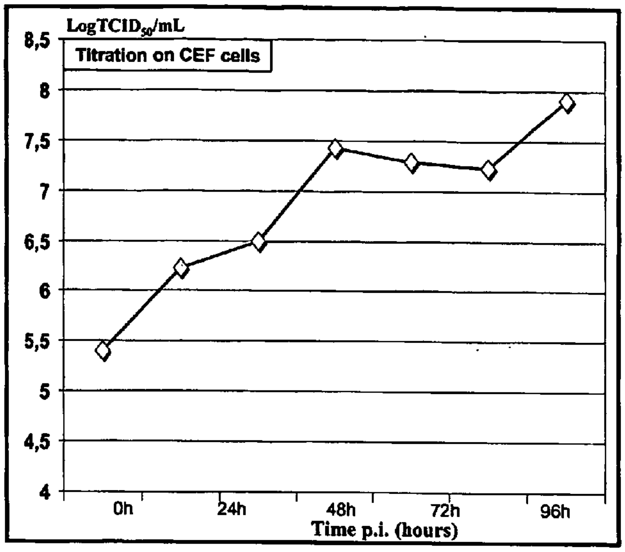

FIG. 16: MVA replication on suspension EB14 cells on a serum-containing medium (MOI: 0.2)

Figure 17:
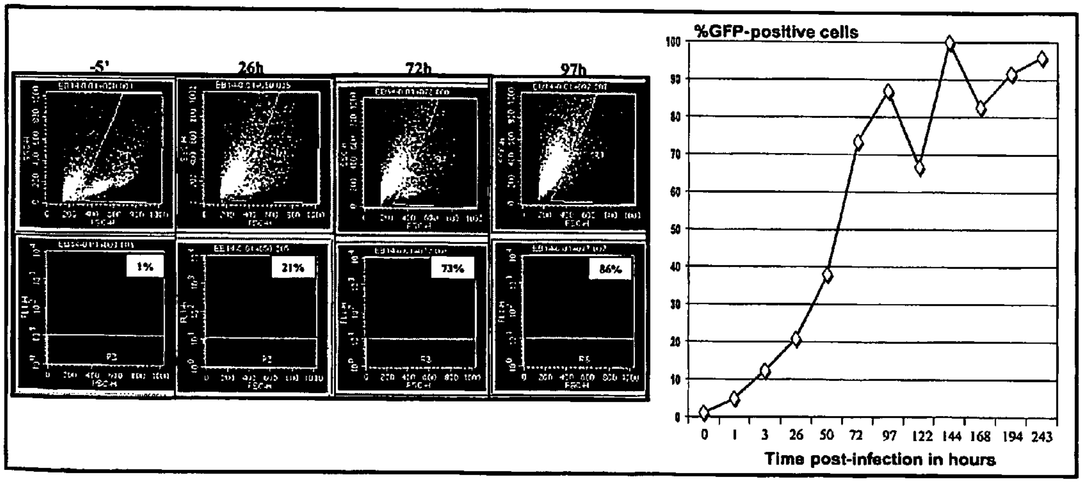

FIG. 17: MVA replication on suspension EB14 cells grown in serum-free medium (MOI: 0.01)

Figure 18:
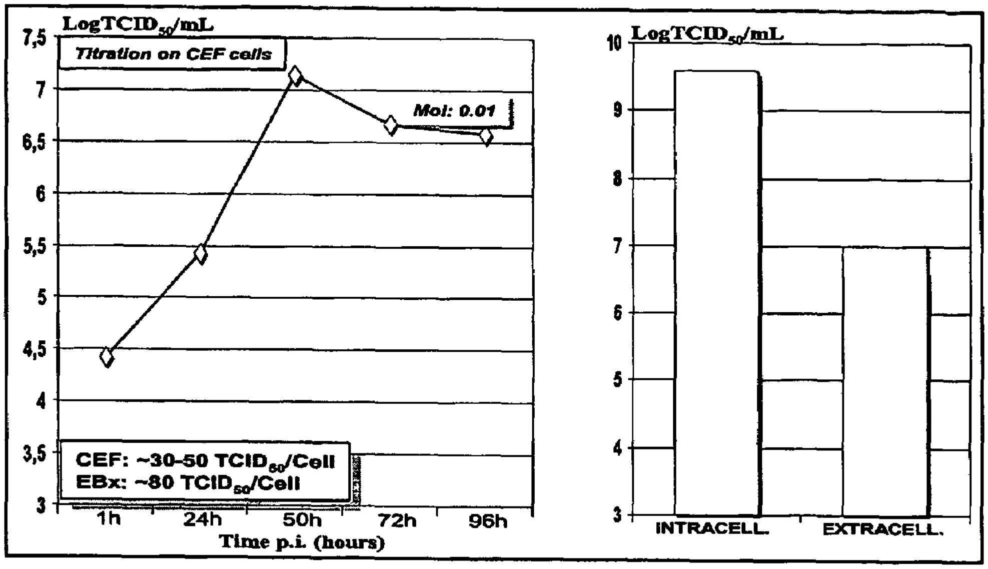

FIG. 18: MVA yields on suspension EB14 cells grown in serum-free medium (MOI: 0.01)

EXAMPLES

Example 1

Production and Establishment of the Adherent Cells

The eggs are opened, the yolk is separated from the egg white during the opening. The embryos are removed from the yolk either directly or with the aid of a Pasteur pipette, or with the aid of a small absorbent filter paper (Whatmann 3M paper), cut out beforehand in the form of a perforated ring with the aid of a punch. The diameter of the perforation is about 5 mm. These small rings are sterilized using dry heat for about 30 minutes in an oven. This small paper ring is deposited on the surface of the yolk and centered on the embryo which is thus surrounded by the paper ring. The latter is then cut out with the aid of small pairs of scissors and the whole removed is placed in a Petri dish, filled with PBS or with a physiological saline. The embryo thus carried away by the ring is cleaned of the excess yolk in the medium and the embryonic disk, thus freed of the excess vitellin, is collected with a Pasteur pipette.

In both cases, the embryos are placed in a tube containing physiological medium (1×PBS, Tris Glucose, medium, and the like). The embryos are then mechanically dissociated and inoculated on a "feeder" into defined culture medium. Among the preferred conditions used for the culturing, preference is given to the culture medium composed of MacCoy or DF12 medium as basal medium supplemented with fetal calf serum at an initial concentration of 12 to 8%, with nonessential amino acids at 1%, with a mixture of vitamins of commercial origin at 1%, with sodium pyruvate at a final concentration of 1 mM, with beta-mercaptoethanol at a final concentration of 0.2 mM, glutamine at a final concentration of 2.9 mM, with an initial mixture of antibiotics containing gentamycin at a final concentration of 10 ng/ml, penicillin at a final concentration of 100 U/ml and streptomycin at a final concentration of 100 μg/ml. Rapidly after the first passages of the cells, the mixture of antibiotics is no longer added to the medium. The expression rapidly is understood to mean after the first 3 to 5 passages in general. A mixture of nucleosides may also be added, this mixture being prepared as described above (Pain et al., 1996). Among the basal media tested under these same conditions and which give similar results are the HamF12, Glasgow MEM and DMEM media, the latter supplemented with biotin at a final concentration of 8 mg/l. By way of comparison, the biotin concentration is 0.2 mg/l in the MacCoy medium, 0.0073 mg/l in the HamF12 and 0 in the commercial DMEM and GMEM media.

The growth factors and the cytokines added to the culture medium are preferably factors and cytokines which are recombinant, including mouse SCF at a final concentration of 1 ng/ml, IGF-1 at a final concentration of 1 to 5 ng/ml, CNTF at a final concentration of 1 ng/ml, IL-6 at a final concentration of 1 ng/ml, and the soluble IL-6 receptor at a final concentration of 0.5 ng/ml to 1 ng/ml. In some experiments, some other factors may be added during the first passages. For example up to passage 3 or 10, it is possible to add bFGF to the medium at a final concentration of 1 ng/ml and IL-11 at a final concentration of 1 ng/ml.

The inoculation is carried out into this medium on the inactivated "feeder" composed of mouse fibroblasts established as lines, the STO cells. In some cases, these cells were transfected with simple expression vectors allowing the expression of growth factors such as avian SCF, constitutively in the STO cells. Thus, this "feeder" produces the factor in a form which is soluble and/or attached in the plasma membrane of the cells.

After initial inoculation of the cells directly into this medium, fresh medium can be added or the medium can be partially changed the next day, and then partially or completely during subsequent days, depending on the rate of adhesion observed for the primary cells. After about 4 to 7 days depending on the cases, the initial culture is dissociated and transferred into new dishes in the same initial medium on the inactivated feeder. After three to five passages, the cells are cultured on an inactivated feeder of STO cells which are non-transfected or transfected with an expression vector encoding a resistance to an antibiotic such as the gene for resistance to neomycin, to hygromycin, to puromycin and the like. After about twenty passages, the cells are progressively deprived of growth factors and cytokines. The expression "gradual withdrawal" is understood to mean a removal growth factor by growth factor, or group of growth factors by group of growth factors, from the culture medium. In the first embodiment, at one passage, SCF is first of all removed, and then, two or three passages later, another growth factor such as IGF-1 for example. If the cells do not exhibit morphological alterations or a variation in their average rate of proliferation, the other factors, such as CNTF and IL-6, are then removed. In a second preferred embodiment, the withdrawal of growth factors is performed group of growth factors by group of growth factors. A first group of growth factors composed by SCF, IL6, IL6R and IL11 is removed then the second group composed of IGF1 and CNTF. In a third embodiment, this withdrawal may also be drastic. All the factors are in this case removed all at once. The cells are then observed and are only passaged several days later if their rate of proliferation is modified. The latter solution is generally that which is practiced.

Various isolates are thus obtained and maintained for very long periods of time. The expression very long periods of time is understood to mean periods of the order of several weeks with a minimum of 50 days, preferably periods greater than 200 to 400 days, without limitation in time. Periods greater than 600 days are observed.

Regardless of the support used, all the cells which are adherent are dissociated with a proteolytic dissociation enzyme, such as pronase, collagenase, dispase, trypsin, and the like. Preferably, a proteolytic enzyme of bacterial origin is used in order to avoid any potential contaminant of animal origin. These cells have the characteristics of embryonic stem cells with a specific morphology illustrated, by way of example, by the photograph of FIG. 8 i.e. a small size, a large nucleo-cytoplasmic ratio, a nucleus with at least one nucleolus which is clearly visible and a very small cytoplasm. These cells are characterized by growth in the form of more or less compact solid masses. The adherent and non-adherent cells exhibit cross-reactivity with a number of antibodies, as described above in Pain et al. (1996) and in patents U.S. Pat. No. 6,114,168 and EP787,180. The endogenous telomerase activity component is also present and is an important factor in the "stem" nature of these cells.

Cells of different isolates are obtained and maintained for long periods of time. Table 1 illustrates a few of the characteristics of these isolates.

TABLE 1

| Name | Species | Start | Stoppage | Days | Passage | Generation |
|---|---|---|---|---|---|---|
| S86N16 | Chicken S86N | 26-01-2000 | 05-08-2001 | 559 | 207 | 692 |
| WL3 | Chicken WL | 28-06-2000 | 09-08-2001 | 403 | 153 | 333 |
| Valo4 | Chicken Valo | 26-09-2000 | 07-02-2002 | 401 | 135 | 317 |
| S86N45 | Chicken S86N | 29-01-2001 | 12-11-2001 | 287 | 118 | 329 |

It will be noted that the term "stoppage" does not correspond to the end of the proliferation of the cells but to a deliberate stoppage of the cell cultures by the experimenter. The number of generation n is obtained by the formula $X=2^n$ or X is the theoretical cumulative number of cells. This number is available since the cells are counted at each passage and during each inoculation. The complete history of the culture is thus available. S86N45 cells also named EB45.

Example 2

Passage of the Cells

One of the characteristics of stem cells, in particular somatic stem cells and embryonic stem cells, is their capacity to proliferate in vitro for considerable periods of time. In order to propagate and to passage the cells, the culture medium is changed and replaced with fresh medium a few hours before their passage. The curve presented in FIG. 1 illustrates a profile of cell growth and establishment.

Example 3

Doubling Time and Average Division Time 3.1 Starting with the established cells in culture and the cells presented in the preceding examples, a mean division time can be calculated. For all the independent isolates obtained, the rate of proliferation increases slightly during successive passages, thus causing the average division time during the establishment of the cells to vary. In the adherent phase, the cells are initially inoculated on an inactivated feeder layer and are passaged regularly at a constant initial inoculation density of 1 to $2\times10^6$ cells per 100 mm dish (55 $cm^2$ dish). Table 2 illustrates the doubling time (d) and the mean division time (MDT in hour) for 3 established cell types as a function of the culture time. It is observed that the mean doubling time decreases during the establishment.

TABLE 2

| Cells/days | 50 | 100 | 150 | 200 | 250 | 300 | 350 | 400 | 450 | 500 | 550 |
|---|---|---|---|---|---|---|---|---|---|---|---|
| S86N16 (d) | 0.30 | 0.63 | 1.00 | 0.86 | 1.13 | 1.15 | 1.47 | 1.70 | 1.94 | 1.50 | 1.9 |
| S86N16 (MDT) | 80 | 38 | 24 | 27.9 | 21.2 | 20.9 | 16.3 | 14.1 | 12.4 | 16 | 12.6 |
| S86N45 (d) | 0.49 | 0.89 | 0.89 | 1.45 | 2.15 | x | x | x | x | x | x |
| S86N45 (MDT) | 49 | 26.8 | 27 | 16.5 | 11.1 | x | x | x | x | x | x |
| Valo4 (d) | 0.03 | 0.61 | 1.00 | 1.17 | 1.26 | 1.03* | 1.08* | 1.25* | x | x | x |
| Valo4 (MDT) | >48 | 39.3 | 24 | 20.5 | 19 | 23.3 | 22.2 | 19.2 | x | x | x |

The mean doubling time d is established for the period of time indicated in days with the following formula: d=(1/Log 2×(Log X2/X1))×1/(T2−T1) where X2 and X1 are total numbers of cells at the times T2 and T1. This formula is the direct consequence of the calculation of the number of generations N by the formula $X=2^n$ presented in example 1. The mean division time (MDT) is then obtained in hours by dividing 24 hours by d.

*The Valo cells are passaged during this establishment on a plastic support without the presence of a feeder. The doubling time decreases and then increases again, when the cells become rehabituated to this new environment.

3.2—Chickens have a body temperature of 39° C. Analysis of S86N45 (EB45) and EB14 cells cell growth kinetics was thus initially performed at 39° C. Under these conditions cells were characterized by a very short generation time usually comprised between 15 to 20 hours (FIG. 2).

Example 4

Cell Culture Temperature

The very rapid cycling of S86N45 (EB45) and EB14 cells at 39° C. may be sub-optimal for efficient MVA virus production. Cell growth at 37° C. and 35° C. was therefore also analyzed (FIG. 3). As expected, cell cycling is reduced at 37° C. Such conditions should in principle be more adequate for virus propagation and will thus be selected in the MVA experiments described below. It is relevant to note that S86N45 (EB45) and EB14 cells can also be grown at 35° C., albeit with a much reduced kinetics. Adaptation of S86N45 and EB14 cells to low temperature (35° C. and even 33° C.) is particularly useful for the production of live attenuated thermo-sensitive viral vaccines.

Example 5

Control of the Level of Serum for the Proliferation of the Lines 5.1—Medium with Low-serum Concentration During the obtaining of these lines, the culture media used are conventional culture media comprising a base (DMEM, GMEM, HamF12, McCoy, and the like) supplemented with various additives such as non-essential amino acids, vitamins, and sodium pyruvate. This complex medium comprises fetal calf serum, which remains a central component of the culture, even though components of different origins, including plant components, can be gradually used. A process for controlling and habituating the cells to relatively low proportions of fetal calf serum is presented. It is thus possible to maintain cells in high proliferation (division time >1) with low percentages of serum (2% for example in the case of the S86N16 cells).

The curves presented in FIG. 4 illustrates the relative reduction of serum for a given cell type: S86N16 cells, The doubling time and the mean division times were also calculated and presented in table 3. It will be noted that the mean division time increases as a function of the relative reduction in serum. A recovery phase is nevertheless observed after some time in culture under the conditions mentioned. This time remains nevertheless less than 24 h (d>1), which already represents a very advantageous proliferation in industrial terms even at serum concentrations of 2%, which is already relatively low. Improvements with regard to the different metabolites to be used may be envisaged in order to increase this time and still further optimize the culture conditions.

TABLE 3

Doubling time and mean division time for S86N16 cells

| | Condition | | | |
|---|---|---|---|---|
| | 10% | 7.5% | 3.75% | 2% |
| d | 2.02 | 1.51 | 1.47 | 1.08 |
| MDT | 11.9 | 15.8 | 16.3 | 22.2 |

The examples are taken between passages p204 and p179 for the 10% condition, between p198 and p176 for the 7.5%, between p224 and p201 for the 3.75% and between p216 and p199 for the 2%.

5.2—Adaptation to Serum-free Medium & Growth in Bioreactors

A major further improvement was achieved by the adaptation of S86N45 (EB45) and EB14 cells to serum-free medium. Several formulations have been tested and a couple of serum-free medium formulations have been identified that allow the efficient growth of S86N45 (EB45) and EB14 cells (FIG. 5).

In addition, the culture of EB14 cells in serum-containing and serum-free media could be further up-scaled since efficient growth was reproducibly demonstrated in 2 L bioreactors (FIG. 6). In addition, EB14 cells can also be efficiently grown in 3L stirred-tank bioreactors and reach densities over 2 millions cells/ml.

Example 6

Deprivation of the Cells of Feeder Layer

Under the initial culture conditions, the presence of a layer of inactivated cells appears to be necessary in order to obtain embryonic stem cells as was described above. This feeder layer no longer appears to be necessary after a number of passages. Only the “culture treated” plastic appears to be important. Indeed, one of the characteristics of some eukaryotic cells is to proliferate in adherent form. In order to facilitate the adhesion of the cells, the various plastic materials used are “culture” treated. They undergo during their manufacture a treatment which adds charges at the surface of the plastic, which charges promote the adhesions of the extracellular matrix of the cells. By contrast, the cell culture untreated plastic, often called plastic of bacteriological quality, is not surface treated by addition of specific feeders. The adhesion of the cells thereto is generally very difficult, or even impossible, or then induces changes in morphology, and in behavior which are often drastic. This distinction between the two plastic qualities makes it possible to obtain, depending on the inoculations which are carried out therein, cells with different behaviors. Gradual deprivation of the cultures of inactivated “feeder” makes it possible to obtain, after a few passages, homogeneous cultures of stem cells directly inoculated on “culture treated” plastic.

The comparative growth curves for the cells maintained in the presence and in the absence of inactivated “feeder” are presented with the case of the S86N16 cells in FIG. 7. This adaptation of the cells is progressive so as not to lose the stem cell character of the cells initially maintained on a “feeder”. Progressive derivatives are thus made. The obtaining of cells which proliferate on plastic is the accomplishment of the withdrawal process. In table 4, the division times show sensitivity of the cells to their environment. As in the case of the progressive withdrawal of serum, an adaptation is obtained with a recovering effect on the cells after a few passages under the conditions defined.

TABLE 4

| | Condition | | | |
|---|---|---|---|---|
| | 1.2 | 0.5 | 0.3 | plastic |
| d | 1.95 | 1.84 | 1.39 | 1.42 |
| MDT | 12.3 | 13 | 17.3 | 16.9 |

The examples are taken between the passages p154 and p131 for the 3 conditions $1.2\times10^6$, $0.5\times10^6$ and $0.3\times10^6$ feeder cells and between p161 and p139 for the condition on plastic alone.

Example 7

Deprivation of the Cells in Growth Factors

Under the initial culture conditions, the presence of growth factors is necessary. It is possible to schematically distinguish two families of factors: the cytokines and the trophic factors.

The cytokines are mainly cytokines whose action is through a receptor which is associated with the gp130 protein. Thus, LIF, interleukin 11, interleukin 6, CNTF, oncostatin and cardiotrophin have a similar mode of action with the recruitment at the level of the receptor of a specific chain and the combination of the latter with the gp130 protein in monomeric or sometimes heterodimeric form. In a few cases, the combination of a soluble form of the receptors, a form described inter alia for the receptors for interleukin 6 and CNTF, makes it possible to increase the proliferative effect observed. It has been previously shown that the addition of at least one of these cytokines appeared to be necessary for obtaining embryonic stem cells.

The trophic factors are mainly SCF, IGF-1 and bFGF, which are also used at the start of the culture, as described above. Their presence is also necessary for obtaining and amplifying the cells.

By progressively reducing these growth factors, it is possible to obtain, after a few passages, culture conditions which allow the proliferation of the embryonic or somatic stem cells without the addition of an exogenous growth factor. The different markers used to characterize these cells are always positive for the cells maintained with no factors.

Example 8

Comparison of the Media Used

Inoculated into different media, the cells are not obtained with the same frequencies. Comparison of the compositions of the media makes the identification of one of the components in particular difficult. It appears more likely that the whole combination allows an improvement in the physiology of the cells. Among the preferred media, the Ham F12 medium, the MacCoy medium, the DMEM medium, DMEM-F12 medium and a DMEM medium enriched with biotin will be noted. Starting with such an isolate, adaptation trials are carried out in these different media.

Example 9

Establishment of the Non-adherent Cells

During the successive passages of the stem cells, a high-density inoculation directly into the bacteriological dish makes it possible to obtain, after a few passages, embryonic cells which become detached from their substrate and which proliferate in suspension in the form of small regular aggregates. This proliferation is encouraged over several passages by more dilution, mechanical dissociation and non-use of proteolytic enzyme. The stirring of the cultures is generally carried out but does not represent a distinguishing factor for obtaining non adherent cells. Like the adherent cells, these cells have a characteristic morphology of stem cells, i.e. a small size, a large nucleo-cytoplasmic ratio, a nucleus with at least one nucleolus which is clearly visible and a small cytoplasm. These cells are characterized by a growth in small aggregates which are more or less compact (FIG. 8). These non adherent cells exhibit cross-reactivity with a number of antibodies, as described above in Pain et al. (1996). These cells are also positive for the endogenous telomerase activity (as presented in example 10 for the EB1, EB4 and EB5 cells). In a non adherent phase, the cells exhibit a high proliferation in different media. The initial inoculation density and the very regular supply of fresh medium provides high densities which may range above $1\times10^6$ cells per ml. Table 5 summarizes the main characteristics of a few isolates (parental cells, initial passage of the making into a suspension, number of days maintained in culture in suspension, number of passages and of generations obtained before voluntary stoppage of the maintenances). It can thus be noted that the passage for the making into a suspension can vary from one isolate to another (see isolate EB1 and EB14) and the proliferation rate (see isolate EB3 and EB14).

TABLE 5

| Name | Parental cells | Initial passage | Start | Days | Passages | Generations |
|---|---|---|---|---|---|---|
| EB1 | S86N16 | p111 | 20-01-2001 | 184 | 41 | 120 |
| EB3 | S86N16 | p118 | 23-01-2001 | 381 | 17 | 40 |
| EB4 | S86N45 | p100 | 25-09-2001 | 44 | 17 | 40 |
| EB5 | S86N45 | p100 | 25-09-2001 | 44 | 17 | 40 |
| EB14 | S86N45 | p81 | 05-09-2002 | 70 | 24 | 65 |

It will be noted that the term "start" corresponds to the cells being placed under non-adherence.

We also found that the obtention of non adherent cells is possible after several passages, at any moment, from adherent stem cells that proliferate with or without feeder layer.

Example 10

Characterization of the Established Cells

The stem cells maintained for long culture times are characterized with the same criteria as those described above (Pain et al., 1996). It is thus possible to regularly detect the endogenous alkaline phosphatase activity, illustrated by the photograph of FIGS. 9*a*-9*b*, the endogenous telomerase activity (FIG. 9*c*) and reactivity with specific antibodies such as the antibodies SSEA-1 (TEC-01) and EMA-1.

One of the important criteria during the establishment of the cells is the presence of telomerase. Various tests were carried out during the maintenance of the cells in culture using a TRAP detection kit (Telomerase PCR Elisa, Roche). The cells are detected positive after various passages in culture. Thus, the telomerase activity is detectable for the S86N16 cells, the S86N45 (EB45) cells and for the EB1, EB4 and EB5 cells which are derived therefrom in a non adherent form (see table 6). The CEFs (Chicken Embryonic Fibroblasts) maintained in primary culture are considered as negative. The threshold of an OD<0.2 is the threshold recommended by the kit as the negative threshold. All the analyses were carried out on an equivalent of 2000 cells.

TABLE 6

Assay of the telomerase activity in various lines at various passages

| Cells | Passage | Telomerase OD |
|---|---|---|
| S86N16 | p12 | 1.7 |
| | p29 | 2.8 |
| | p185 | 0.97 |
| | p204 | 0.95 |
| S86N16 EB1 | p134 | 1.1 |
| S86N45 (EB45) | p50 | 0.87 |
| | p58 | 1.1 |
| | p66 | 0.96 |
| | p94 | 1.2 |
| EB4 | p112 | 1.4 |
| EB5 | p112 | 0.94 |
| CEF* | p4 | 0.07 |

*CEF: Chicken Embryonic Fibroblast

Figure 9C:
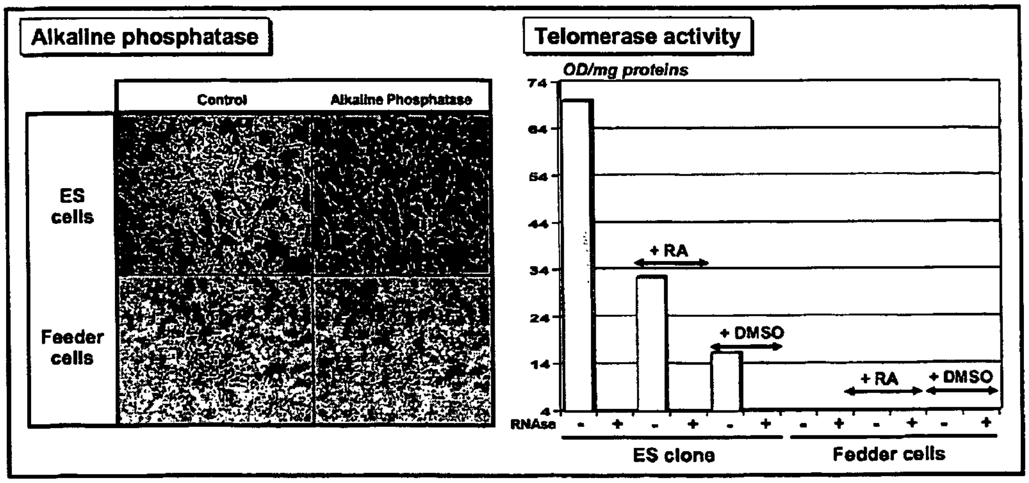

Of particular importance, the cells of the invention have conserved some essential "stem cell" features. They express a series of stem cell-specific markers known to be present in mouse, chicken and human embryonic stem cells (eg. Alkaline phosphatase, SSEA-1, EMA-1, telomerase) (FIG. 9). As expected, expression of these markers is lost upon experimental induction of cell differentiation by addition of retinoic acid (RA) or DMSO (Table 7 and FIG. 9*c*). They replicate indefinitely in vitro (FIG. 1); several candidate cell lines have been cultured for more than a year without specific hurdles, such as differentiation.

TABLE 7

ES cell-specific markers: "markers expression is decreased upon differentiation with retinoic acid"

| MARKERS | WITHOUT RETINOIC ACID | WITH RETINOIC ACID |
|---|---|---|
| Alcaline Phosphatase | ++++ | – |
| SSEA-1 | 90 | <10 |
| EMA-1 | 90 | 10 |
| Telomerase Activity (OD) | >1.5 | <0.2 |

The markers SSEA1 and EMA1 are expressed in percentage of labelled cells.

Example 11

Transfection and Induction of the Cells

The stem cells maintained in a growth over the long term are transfected with various expression plasmids. It has been shown that avian stem cells could be transfected (Pain et al., 1996). In particular, the non adherent cells are transfected and various sorting systems make it possible to identify the stably transfected cells (cell sorting, limiting dilution, and the like). These genetic modifications can be made at the undifferentiated stage of the stem cell. Once this modification has been obtained, the cell is then induced to differentiate spontaneously or by addition of a differentiation inducer. In this case, it is possible to use retinoic acid at concentrations of $10^{-8}$ M to $10^{-6}$ M, or dimethyl sulfoxide at concentrations of 1 to 2% final or sodium butyrate at concentrations of $10^{-4}$ to $10^{-8}$ M, or phorbol ester (TPA, PMA, and the like) or lipopolysaccharides (LPS) at concentrations of 1 to 5 μg/ml final. In another example, the cells can form embryoid bodies in suspension, which embryoid bodies can be caused to adhere to plastic after dissociation or nondissociation of the cells constituting them. These differentiated cells then proliferate but have a more limited capacity for proliferation over the long term. By targeting the genetic modification on a gene which influences the proliferation of the cells, it is possible to make these differentiated cells capable of proliferating over the long term.

Example 12

Protocol for Infecting a Non Adherent Avian Cell Line (EB1) with a Virus

Amplification of the Cells:

The EB1 or EB14 cells are inoculated into a medium, preferably MacCoy's 5A, HAMF12 or DMEM medium, or any other medium of interest, containing 5% serum at a concentration of $0.2\times10^6$ cells/ml for an initial volume of 50 ml in general. They are maintained in culture at 39° C. and at 7.5% $CO_2$, with stirring. Fresh medium is added every day for the 3 to 4 days for which the amplification lasts in order to reach a cell concentration of 1 to $3\times10^6$ cells/ml for a final culture volume of 100 to 250 ml.

The cells in suspension are collected and centrifuged for 10 min at 1 000 rpm approximately. The pellet is resuspended in 20 to 50 ml of 1×PBS (Phosphate buffer Salt). The cells are then counted, centrifuged and the pelleted cells are taken up in a serum-free medium at a final concentration of 3 to $5\times10^6$ cells/ml. Several tubes are then prepared under these conditions containing 3 to $5\times10^6$ cells per tube.

Preparation of the Virus and Infection:

The viral stock having a known titer is rapidly thawed at 37° C. and diluted in serum-free medium at a titer of 10× to 1000× the concentration necessary for the final infection. The cells are infected with the virus of interest at an m.o.i. (multiplicity of infection) of 0.01 to 0.5 according to the types of virus, which involves adding between 0.1 and 10% volume/volume of viral suspension to the cellular pellet. After incubating for 1 hour at an optimum temperature for the virus, in general from 33 to 37° C., the cells are again centrifuged and the medium removed with care. This step is found to be often necessary in order to limit the effect of the initial virus in the subsequent process. One of the possibilities is to directly dilute the cells without centrifuging them again with serum-containing medium (5% of serum) at a final concentration of 0.2 to $1\times10^6$ cells/ml and incubated again.

Harvesting of the Supernatant and of the Cells:

After 2 to 4 days of incubation, depending on the viral kinetics and the potential cytopathic effect of certain viruses, the medium containing the cells or the cellular debris is harvested.

Depending on the viruses, only the pellet or the supernatant may be of interest and contain the viral particles. The cells are harvested and centrifuged. The collected supernatant is centrifuged again for 5 to 10 minutes at 2 500 rpm, and stored at −80° C. before purification of the particles. An aliquot is collected in order to carry out the titration. The cellular pellet is taken up in 5 ml of serum-free medium, sonicated and centrifuged for 5 to 10 minutes at 2500 rpm. The supernatant obtained is stored at −80° C. up to the purification and the titration of an aliquot.

The viral infection and production efficiencies are compared between the various conditions performed. For the viruses with cytopathic effects, the titrations are in general carried out by the lysis plaque technique.

Example 13

Protocol for Infecting an Adherent Avian Cell Line (S86N45) with a Virus

Preparation of the Cells:

The cells are inoculated 48 hours before the infection into T150 flasks at a concentration of between 0.03 and $0.06\times10^6$ cells/$cm^2$ in a medium, preferably MacCoy's 5A, HAMF12 or DMEM medium, or any other medium of interest, containing 5% serum. They are maintained at 39° C. and 7.5% $CO_2$.

Infection:

The viral stock having a known titer is rapidly thawed at 37° C. and diluted in serum-free medium at a titer of 10× to 1 000× the concentration necessary for the final infection. The cells are infected with the virus of interest at an m.o.i. (multiplicity of infection) of 0.01 to 0.5 according to the types of virus, which involves adding between 0.1 and 10% volume/volume of viral suspension to the cell monolayer. The infection is generally carried out in a minimum of medium (from 5 to 10 ml for a 75 $cm^2$ flask) in a medium containing 0% serum. After incubating for I hour at the optimum temperature for the virus, in general from 33 to 37° C., 20 ml of medium 5% are added to the flasks. In a particular case, the cells can be washed with PBS in order to remove the particles which might be attached to the cells. In the case of a cytopathic virus, the cells are observed daily after the infection in order to monitor the appearance of cell lysis, which indicates good progress of the infection.

Harvesting of the Supernatant and of the Cells:

After 2 to 4 days of incubation, depending on the viral kinetics and the potential cytopathic effect of certain viruses, the medium containing the supernatant, the cells and the cellular debris are harvested. Depending on the viruses, only the pellet or the supernatant may be of interest and contain the viral particles. The cells are harvested and centrifuged. The collected supernatant is centrifuged again for 5 to 10 minutes at 2500 rpm, and stored at −80° C. before purification of the particles. An aliquot is collected in order to carry out the titration. The cellular pellet is taken up in 5 ml of serum-free medium, sonicated and centrifuged for 5 to 10 minutes at 2500 rpm. The supernatant obtained is stored at −80° C. up to the purification and the titration of an aliquot.

The viral infection and production efficiencies are compared between the various conditions performed. For the viruses with cytopathic effect, the titrations are in general carried out by the lysis plaque technique.

Example 14

Replication of Modified Vaccinia Virus Ankara (MVA) on Adherent and Non-adherent Avian Stem Cells of the EB45 Line and EB14 Line A series of experiments was performed on the EB45 (S86N45) and EB14 cells to determine their respective susceptibilities to MVA infection, the kinetics of MVA propagation, and the viral production yields. The MVA viruses used in these studies were either a recombinant MVA vector expressing the reporter GFP protein (MVA-GFP) or a non-recombinant MVA virus. Freshly prepared chicken embryonic fibroblasts (CEF) were included in all experiments as control cells.

14.1—Safety Consideration

The MVA virus (titer $2.5\times10^7$ TCID50/ml in 0.5 ml vials) was received under frozen conditions. For safety reasons, the MVA virus and infected cells were kept under controlled conditions (−80° C. freezer) and the contaminated plastic material was placed into hypochloride solution for more than 1 hour and then place into a bag for full and complete autoclave inactivation.

14.2—Virus Production 14.2.1—Adherent S86N45 (EB45) Cells $1\times10^6$ adherent cells are seeded in 100 mm dish the day before infection, in 20 mL medium. 24 hours later, the medium is discarded, cells are incubated at 37° C. with the inoculum (2 mL serum-free medium, at a multiplicity of infection of 0.01 or 0.1 TCID/cell). 1 hour later, the inoculum is discarded, and 20 mL of pre-warmed medium is added to the cells, and the incubation is kept at 37° C. in 5% $CO_2$. For virus preparation, the infected cells are harvested by scrapper, transferred in a 50 mL Falcon™ tube and spun at 1200 RPM at room temperature. The supernatant (extracellular viruses, EV) is collected, and the cell pellet (intracellular viruses, IV) is diluted in 1 or 2 mL of medium. EV and IV samples undergo both three thawing-freezing cycles, and then they are sonicated. After centrifugation at 2500 rpm for 10 mn at room temperature, EV and IV samples are aliquoted and kept at −80° C. until titration.

14.2.2—Suspension EB14 Cells $0.4\times10^6$/mL EB14 cells are seeded in 40 mL medium ($16\times10^6$ cells) in 125 mL spinner bottles the day before addition of the viral inoculum, at a moi of 0.01 or 0.1 TCID/cell in the medium. After one hour of virus incubation, 80 mL of pre-warmed medium is added. Incubation is kept at 37° C. under wished spin conditions and 5% $CO_2$. Infected cells are then harvested at various times post-infection, transfered in 50 mL Falcon™ tubes and spun at 1200 RPM at room temperature. The supernatant (extracellular viruses, EV) is collected, and the cell pellet (intracellular viruses, IV) is diluted in 5 or 10 mL of medium. EV and IV samples undergo both three thawing-freezing cycles, and then they are sonicated. After centrifugation at 2500 rpm for 10 mn at room temperature, EV and IV samples are aliquoted and kept at −80° C. until titration.

14.3—Virus Titration 14.3.1—Titration of MVA by the $TCID_{50}$ End-point Dilution Method The titration of MVA viruses are done by the $TCID_{50}$ end-point dilution method on CEF or DF-1 cells. The assay determines that the sample contains a sufficient dose of infectious virus to produce infection. $TCID_{50}$ is determined as the dilution that produced cytopathic effect (CPE) in one-half of the cumulative number of cell cultures. One P96 flat bottom is needed for one viral sample titer. Briefly, 15000 CEF cells/100 µL are seeded per well. Eight rows of eleven wells are seeded. The eight rows stand for the height serial 10-fold dilutions of the viral sample (i.e. $10^{-2}$ to $10^{-9}$). For each serial dilution, a 1 mL mix is done in serum-free medium, 100 µL of the mix is dispensed in 10 corresponding dilution-wells, and the eleventh row is the control non-infected well. The P96 plate is incubated at 37° C. in 5% $CO_2$. Between 5 to 10 days later, the viral titer is calculated by the Reed-Muench method by recording the positive CPE wells.

14.4—Results of the Susceptibility to MVA Infection and Titration 14.4.1—The intrinsic susceptibility of EB45 (S86N45) and EB14 cells to MVA infection was first investigated using the recombinant MVA-GFP vector. This specific vector was selected for these studies to simplify the monitoring and quantification of the infected cells. EBx and CEF cells were thus treated with different multiplicities of infections (moi) and cells were analysed by fluorescence microscopy and fluorocytometry at several days post-infections.

As shown in FIGS. 10 and 11, all adherent EB45 cells that are still viable at 48 hours post-infection did strongly express the reporter GFP protein, even when using a moi as low as 0.1 $TCID_{50}$s/cell. Of note, FIG. 10 also illustrates the much smaller size of EB45 and EB14 cells when compared to CEF cells.

Altogether, these results clearly demonstrate the high susceptibility of the adherent EB45 and EB14 cells to MVA infection.

14.4.2—The following table 8 lists results obtained in the various MVA-GFP infection experiments performed. All samples were tittered twice.

TABLE 8

Results of the titration

| Experimental conditions | Multiplicity of infection (MOI) | Time post-infection (PI) (in hours) | Titration (in $TCID_{50}$/ml) |
|---|---|---|---|
| S86N45 (EB45) cells | 0.01 | 96 | 9.57 |
| in DMEM-F12 | | 96 | 8.57 |
| medium (100 mm | 0.1 | 72 | 7.5 |
| diameter dish) | | 72 | 7.63 |
| EB14 cells in | 0.2 | 48 | 7.5 |
| DMEM-F12 medium | | 72 | 7.63 |
| (120 ml spinner flasks) | | | |
| CEF cells in HAM- | 0.01 | 96 | 7.5 |
| F12 medium (100 mm | | 96 | 7.71 |
| diameter dish) | 0.1 | 72 | 7.39 |
| | | 72 | 7.91 |

14.3—Propagation of MVA on EB14 and EB45 Cells

Propagation of MVA on the suspension EB14 and adherent EB45 cells was determined by a quantitative analysis of the kinetics of MVA-GFP replication. EB45 cells were grown in dishes in DMEM-F12 medium and were infected with a moi of 0.1, while EB14 cells were cultured in 120 ml spinner flasks in DMEM-F12 medium for 24 hours before infection with a moi of 0.2. The percentage of infected cells was then quantified by FACS analysis at various times post-infection. As illustrated in FIGS. 12 and 13, all cells that are still viable do express GFP at 48 hours (EB45) or 72 hours (EB 14) post-infection.

14.4—Viral Yields on Adherent EB45 Cells Grown in Serum-containing Medium 14.4.1—The viral productivity of the adherent EB45 cells was analysed using cells grown in DMEM-F12. MVA was found to be very efficiently replicated in EB45 in DMEM-F12 and to achieve yields higher than the one obtained with control CEF cells (FIG. 14).

14.4.2—In a further series of experiments, a non-recombinant MVA virus (from the ATCC) was used for a comparative replication study on CEF cells and EB45 cells: confirming previous results with the MVA-GFP vector, a higher production yields were again obtained with this MVA virus (FIG. 15).

Altogether, these results demonstrate the high susceptibility to MVA infection and the efficient virus production of the adherent EB45 cells, which are higher than in chicken embryonic fibroblasts. In addition, all these experiments were performed under standard conditions. It is therefore reasonable to argue that even higher virus yields may be achieved upon optimisation of the experimental conditions, and in particular by using optimal cell culture media.

14.5—Viral Yields on Suspension EB14 Cells Grown on Serum-containing Medium

The viral productivity of EB14 cells has been determined in spinner flasks using cells grown in DMEM-F12 medium. Results of a first series of experiments using a multiplicity of infection of 0.1 are shown in FIG. 16. These data support the previous results obtained with the adherent cells and confirm the ability of the suspension EB14 cells to efficiently produce recombinant MVA viruses at yields close to 100 $TCID_{50}$/Cell, two fold higher than the one obtained with chicken embryonic fibroblasts.

14.6—Viral Yields on Suspension EB14 Cells Grown on Serum-free Medium

Ideally, viral vaccines production should be performed on suspension cells grown in serum-free medium in bioreactors. In order to investigate the production of MVA in serum-free media, a series of experiments was initiated in which EB14 suspension cells have been infected with the MVA-GFP vector in spinner flasks in serum-free medium at two different multiplicities of infection (0.01 & 0.1). FACS analyses of the cells confirm the efficient infection of EB14 cells in the two experimental conditions (FIG. 17). In addition, and as expected, these experiments show that infection is more rapid when using an moi of 0.1, while at an moi of 0.01 cells are viable longer and able to produce virus progeny for a longer period of time (data not shown).

Analysis of virus yields confirm that efficient MVA production is achieved by the suspension EB14 cells grown in suspension in serum-free and protein-free medium (FIG. 18). A virus yield higher than the one unusually obtained with CEF cells is routinely obtained. In addition, analysis of the distribution of the infectious particles indicate that most virions are retained within the cells and only a fraction is secreted in the supernatant (FIG. 18).

EB14 and S86N45 cells are well characterized non-genetically engineered avian embryonic stem cells that can be efficiently grown in serum-free medium, either in suspension or as adherent cells. The inventors demonstrate that the cells are highly susceptible to infection and propagation of a recombinant and a non-recombinant modified-vaccinia virus Ankara, and results indicate that viral production is at least two to three fold higher than in control CEF cells. Altogether, these features make of cells of the invention, mainly EB14 and EB45, a highly promising cell substrate to replace the current egg-based or CEF-based production system for the production of MVA-based vectors.

REFERENCES

Baba T W, Humphries E I L (1985). Formation of a transformed follicle is necessary but not sufficient for development of an avian leukosis virus-induced lymphoma. Proc. Natl. Acad. Sci. USA 82: 213-216.

Beug H, von Kirchbach A, Doderlein G, Conscience J F, Graf T. (1979). Chicken hematopoietic cells transformed by seven strains of defective avian leukemia viruses display three distinct phenotypes of differentiation. Cell 18: 375-390.

Guilbot C, Benchaibi M, Flechon J E, Samarut J. (1993). The 12S adenoviral E1A protein immortalizes avian cells and interacts with the avian RB product. Oncogene 8: 619-624

Kawaguchi T, Nomura K, Hirayama Y, Kitagawa T. (1987). Establishment and characterization of a chicken hepatocellular carcinoma cell line, LMH. Cancer Res 1987 47: 4460-4464.

Kim H, You S, Farris J. Foster L K, Foster D N. (2001). Post-transcriptional inactivation of p 53 in immortalized chicken embryo fibroblast cells. Oncogene 20: 3306-3310.

Kim H, You S, Kim I J, Foster L K, Farris J, Ambady S, Ponce de Leon F A, Foster D N. (2001). Alterations in p 53 and E2F-1 function common to immortalized chicken embryo fibroblasts. Oncogene 20: 2671-2682.

Liu J L, Klein P A, Moscovici M G, Moscovici C. (1992). Monoclonal antibodies recognizing normal and retrovirus-transformed chicken hematopoietic cells. Virology 189: 583-591.

Moscovici C, Moscovici M G, Jimenez H, Lai M M, Hayman M J, Vogt P K. (1977). Continuous tissue culture cell lines derived from chemically induced tumors of Japanese quail. Cell 11: 95-103.

Moss B. (1994) Replicating and host-restricted non-replicating vaccinia virus vectors for vaccine development. Dev Biol Stand. 82: 55-63.

Pain B., Clark M. E., Shen M., Nakazawa H., Sakurai M., Samarut J., Etches R J. (1996). Long-term in vitro culture and characterisation of avian embryonic stem cells with multiple morphogenetic potentialities. Development 122: 2339-2348.

Pain B., Chenevier P., Samarut J. (1999). Chicken embryonic stem cells and transgenic strategies. Cells Tissues Organs 165: 212-219.

Samarut J, Gazzolo L. (1982). Target cells infected by avian erythroblastosis virus differentiate and become transformed. Cell 28: 921-929.

Smith J R and Pereira-Smith O M (1996). Replicative senescence: implications for in vivo aging and tumor suppression. Science 273, 63-67.

The invention claimed is:

1. A method for replicating a native or recombinant vaccinia virus comprising the steps of:

1) producing avian embryonic derived stem cells by:

a) culturing avian embryonic cells in a complete culture medium complemented in serum containing:

i) exogenous growth factors comprising the trophic factors SCF, IGF-1 and bFGF, and cytokines whose action is through a receptor which is associated with the gp130 protein, said cytokines being selected from the group consisting of LIF, interleukin 11, interleukin 6, interleukin 6 receptor, CNFT, oncostatin and cardiotrophin; and ii) a feeder layer;

b) passage by modifying the culture medium so as to obtain the withdrawal of said growth factors, of the serum and/or of the feeder layer;

c) establishing adherent or non-adherent cell lines capable of proliferating in a basal medium in the absence of exogenous growth factors, serum and/or inactivated feeder layer;

2) inoculating the resultant avian embryonic derived stem cells with viral particles of said vaccinia virus; and 3) culturing said cells in a basal medium until cell lysis occurs and newly produced viral particles of said vaccinia virus are released in said medium.

2. The method according to claim 1, wherein said avian embryonic cells are chicken or duck embryonic cells.

3. The method according to claim 1, wherein the feeder layer is inactivated.

4. The method according to claim 1, wherein the avian embryonic derived stem cells produced in step 1) are non-adherent stem cells which proliferate in suspension in a medium free of exogenous growth factors, serum and feeder cells.

5. The method according to claim 1, wherein said vaccinia virus is the native Modified Vaccinia virus Ankara (MVA) or a recombinant thereof.

6. The method according to claim 1, wherein the avian embryonic derived stem cells produced in step 1) are capable of proliferating for at least 600 days.

7. The method according to claim 1, wherein the avian embryonic derived cell lines produced in step 1) are non-adherent stem cells which proliferate in suspension in a medium free of exogenous growth factors.

8. The method according to claim 1, wherein the avian embryonic derived cell lines produced in step 1) are non-adherent stem cells which proliferate in suspension in a medium free of serum (serum-free medium).

9. The method according to claim 1, wherein the avian embryonic derived cell lines produced in step 1) are non-adherent stem cells which proliferate in suspension in a medium free of exogenous growth factors and serum.

10. The method according claim 1, wherein the avian embryonic derived cell lines produced in step 1) have at least one of the following characteristics:

a high nucleo-cytoplasmic ratio, an endogenous alkaline phosphatase activity, an endogenous telomerase activity, a reactivity with specific antibodies selected from the group of antibodies consisting of SSEA-1 (TEC01), SSEA-3 and EMA-1.

11. The method according to claim 1, wherein said basal medium is selected from the group consisting of DMEM, GMEM, HamF12 and McCoy basal medium supplemented with additives.

* * * * *